US006379855B1

(12) United States Patent
Hayashi et al.

(10) Patent No.: US 6,379,855 B1
(45) Date of Patent: Apr. 30, 2002

(54) BLACK MAGNETIC TONER AND BLACK MAGNETIC COMPOSITE PARTICLES THEREFOR

(75) Inventors: Kazuyuki Hayashi; Hiroko Morii, both of Hiroshima; Yasuyuki Tanaka, Onoda; Seiji Ishitani, Hiroshima, all of (JP)

(73) Assignee: Toda Kogyo Corporation, Hiroshima-ken (JP)

( * ) Notice: Subject to any disclaimer, the term of this patent is extended or adjusted under 35 U.S.C. 154(b) by 0 days.

(21) Appl. No.: 09/636,224

(22) Filed: Aug. 10, 2000

Related U.S. Application Data

(63) Continuation-in-part of application No. 09/541,725, filed on Apr. 3, 2000, which is a continuation-in-part of application No. 09/248,283, filed on Feb. 11, 1999, now abandoned.

(30) Foreign Application Priority Data

| Feb. 17, 1998 | (JP) | ................................ 10-52826 |
| Aug. 11, 1999 | (JP) | ............................. 11-227825 |
| Apr. 28, 2000 | (JP) | .......................... 2000-131865 |

(51) Int. Cl.$^7$ ................................. G03G 9/083
(52) U.S. Cl. ..................... 430/106.1; 428/405; 428/407
(58) Field of Search ............................. 430/106.6, 108; 428/407, 405, 106.1

(56) References Cited

U.S. PATENT DOCUMENTS 4,161,454 A    7/1979   Lu
4,620,987 A    11/1986  Yamashita et al.
4,937,157 A  *  6/1990  Haack ..................... 430/106.6

FOREIGN PATENT DOCUMENTS

| EP | 0373426      | 12/1988 |
| EP | 0 439 367 A2 | 7/1991  |
| EP | 0 913 431 A2 | 5/1999  |
| EP | 0 936 507 A2 | 8/1999  |

* cited by examiner

Primary Examiner—Christopher Rodee
(74) Attorney, Agent, or Firm—Nixon & Vanderhye

(57) ABSTRACT

Black magnetic toner comprising:
  a binder resin; and
  black magnetic composite particles comprising:
    magnetic iron oxide particles having an average particle diameter of 0.055 to 0.95 $\mu$m,
    a coating layer formed on the surface of the magnetic iron oxide particles, comprising at least one organosilicon compound selected from the group consisting of:
      (1) organosilane compounds obtainable from alkoxysilane compounds, and
      (2) polysiloxanes or modified polysiloxanes, and a carbon black coat formed on the coating layer comprising the organosilicon compound, in an amount of 26 to 55 parts by weight based on 100 parts by weight of the magnetic iron oxide particles.

Such a black magnetic toner can be free from being deteriorated in electric resistance due to the existence of the carbon black coat, and as a result, is suitable as a high-resistant or insulated magnetic toner.

33 Claims, No Drawings

BLACK MAGNETIC TONER AND BLACK MAGNETIC COMPOSITE PARTICLES THEREFOR

CROSS REFERENCE TO RELATED APPLICATION

This is a continuation-in-part of application Ser. No. 09/541,725 filed Apr. 3, 2000, which is a continuation-in-part of application Ser. No. 09/248,283 filed Feb. 11, 1999 abandoned.

BACKGROUND OF THE INVENTION

The present invention relates to a black magnetic toner and black magnetic.composite particles for the black magnetic toner, and more particularly, to black magnetic composite particles for high-resistant black magnetic toner, which are not only more excellent in fluidity and blackness but also show an excellent dispersibility in a binder resin due to a less amount of carbon black desorbed or fallen-off from the surface of each particle; a process for producing the black magnetic composite particles; and a high-resistant black magnetic toner using the black magnetic composite particles which is more excellent in fluidity and blackness.

As one of conventional electrostatic latent image-developing methods, there has been widely known and generally adopted a so-called one component system development method of using as a developer, a magnetic toner comprising composite particles prepared by mixing and dispersing magnetic particles such as magnetite particles in a resin, without using a carrier.

The conventional development methods of using one-component magnetic toner have been classified into CPC development methods of using a low-resistance magnetic toner, and PPC development methods of using a high-resistant magnetic toner.

In the CPC methods, the low-resistance magnetic toner used therefor has an electric conductivity, and is charged by the electrostatic induction due to electric charge of the latent images. However, since the charge induced on the magnetic toner is lost while the magnetic toner is transported from a developing zone to a transfer zone, the low-resistance magnetic toner is unsuitable for the PPC development method of using an electrostatic transfer method. In order to solve this problem, there have been developed the insulated or high-resistant magnetic toners having a volume resistivity as high as not less than $1 \times 10^{13}$ Ω·cm.

As to the insulated or high-resistant magnetic toner, it is known that the developing characteristics thereof are affected by magnetic particles exposed to the surface of the magnetic toner, or the like.

Recently, with the high image quality such as high image density or high tone gradation, or with the high copying speed of duplicating machines, it has been strongly demanded to further enhance characteristics of the insulted or high-resistant magnetic toners as a developer, especially a fluidity thereof.

With respect to such demands, in Japanese Patent Application Laid-Open (KOKAI) No. 53-94932(1978), there has been described "these high-resistant magnetic toners are deteriorated in fluidity due to the high electric resistance, so that there arises such a problem that non-uniformity of developed images tend to be caused. Namely, although the high-resistant magnetic toners for PPC development method can maintain necessary charges required for image transfer, the magnetic toners are frictionally charged even when they are present in other steps than the transfer step, where the magnetic toners are not required to be charged, e.g., in a toner bottle or on the surface of a magnetic roll, or also slightly charged by mechano-electrets during the production process of these magnetic toners. Therefore, the magnetic toners tend to be electrostatically agglomerated, resulting in deterioration of fluidity thereof", and "It is an another object of the present invention to provide a high-resistant magnetic toner for PPC development method which is improved in fluidity, can be prevented from causing non-uniformity of developed images, and has an excellent image definition and tone gradation, thereby obtaining high-quality copies by indirect copying methods".

In recent years, with the reduction in particle size of the insulated or high-resistant magnetic toners, it has been increasingly required to enhance the fluidity thereof.

With respect to such a fact, in "Comprehensive Data Collection for Development and Utilization of Toner Materials" published by Japan Scientific Information Co., Ltd., page 121, there has been described "With extensive development of printers such as ICP, a high image quality has been required. In particular, it has been demanded to develop high-precision or high-definition printers. In Table 1, there is shown a relationship between definitions obtained by using the respective toners. As is apparent from Table 1, the smaller the particle size of wet toners, the higher the image definition is obtained. Therefore, when a dry toner is used, in order to enhance the image definition, it is also required to reduce the particle size of the toner . . . As reports of using toners having a small particle size, it has been proposed that by using toners having a particle size of 8.5 to 11 μm, fogs on a background can be improved and toner consumption can be reduced, and further by using polyester-based toners having a particle size of 6 to 10 μm, an image quality, a charging stability and lifetime of the developer can be improved. However, when such toners having a small particle size are used, it has been required to solve many problems. There are problems such as improvement in productivity, sharpness of particle size distribution, improvement in fluidity, etc.".

Further, black magnetic toners widely used at the present time, have been required to show a high degree of blackness and a high image density for line images and solid area images on copies.

With respect to this fact, on page 272 of the above-mentioned "Comprehensive Data Collection for Development and Utilization of Toner Materials", there has been described "Powder development is characterized by a high image density. However, the high image density as well as the fog density as described hereinafter, greatly influences image characteristics obtained".

There is a close relationship between properties of the magnetic toner and those of the magnetic particles mixed and dispersed in the magnetic toner.

That is, the fluidity of the magnetic toner is largely varied depending upon surface condition of the magnetic particles exposed to the surface of the magnetic toner. Therefore, the magnetic particles themselves have been strongly required to show an excellent fluidity.

The degree of blackness and density of the magnetic toner are also largely varied depending upon the degree of blackness and density of the magnetic particles as a black pigment contained in the magnetic toner.

As the black pigment, magnetite particles have been widely used from the standpoints of magnetic properties such as saturation magnetization or coercive force, low price, color tone or the like. In addition to the magnetite particles, carbon black fine particles may be added. However, in the case where the carbon black fine particles are used in a large amount, the volume resistivity thereof is lowered to less than $1.0 \times 10^{13}$ Ω·cm, so that it is not possible to use the obtained toner as an insulated or high-resistant magnetic toner. Further, the dispersibility of the magnetite particles in the binder resin is deteriorated.

Hitherto, in order to enhance the fluidity of the black magnetic toner, there have been many attempts of improving the fluidity of the magnetite particles mixed and dispersed in the magnetic toner. For example, there have been proposed (1) a method of forming spherical-shaped magnetite particles (Japanese Patent Application Laid-Open (KOKAI) No. 59-64852(1984)), (2) a method of exposing a silicon compound to the surface of magnetite particles (Japanese Patent Publication (KOKOKU) No. 8-25747(1996)), or the like.

Black magnetic composite particles for black magnetic toner, which have not only a more excellent fluidity and blackness, but also an excellent dispersibility in a binder resin, are presently strongly demanded. However, black magnetic composite particles capable of satisfying all of these requirements have not been obtained yet.

Namely, the above-mentioned spherical magnetite particles show a higher fluidity than those of cubic magnetite particles, octahedral magnetite particles or the like. However, the fluidity of the spherical magnetite particles is still insufficient, and further the blackness is disadvantageously low.

As to the above-mentioned magnetite particles to the surface of which the silicon compound is exposed, the fluidity thereof is also still insufficient, and the blackness thereof is also disadvantageously low.

As a result of the present inventor's earnest studies for solving the above problems, it has been found that by using as magnetic particles for a black magnetic toner, black magnetic composite particles having an average particle size of 0.06 to 1.0 μm, comprising: magnetic iron oxide particles as core particles; a coating layer comprising an organosilicon compound which is formed on the surface of each magnetic iron oxide particle; and a carbon black coat formed onto at least a part of the surface of the coating layer in an amount of 26 to 55 parts by weight based on 100 parts by weight of the magnetic iron oxide particles, the obtained black magnetic toner not only exhibits a more excellent fluidity and a more excellent blackness, but also has a high volume resistivity value and, therefore, can realize a high image quality and a high copying speed. The present invention has been attained on the basis of the finding.

SUMMARY OF THE INVENTION

It is an object of the present invention to provide black magnetic composite particles for high-resistant black magnetic toner, which are not only more excellent in fluidity and blackness, but also can show an excellent dispersibility in a binder resin.

It is another object of the present invention to provide a black magnetic toner which is not only more excellent in fluidity and blackness, but also can have a high volume resistivity value.

To accomplish the aims, in a first aspect of the present invention, there is provided a black magnetic toner comprising:

a binder resin, and
black magnetic composite particles having an average particle diameter of 0.06 to 1.0 μm, comprising:
  magnetic iron oxide particles;
  a coating layer formed on the surface of the magnetic iron oxide particle, comprising at least one organosilicon compound selected from the group consisting of:
    (1) organosilane compounds obtained from an alkoxysilane compounds, and
    (2) polysiloxanes or modified polysiloxanes; and a carbon black coat formed on at least a part of the coating layer comprising the organosilicon compound, in an amount of 26 to 55 parts by weight based on 100 parts by weight of the magnetic iron oxide particles.

In a second aspect of the present invention, there is provided black magnetic toner comprising:

a binder resin, and
black magnetic composite particles having an average particle diameter of 0.06 to 1.0 μm, comprising:
  magnetic iron oxide particles;
  a coat formed on at least a part of the surface of the magnetic iron oxide particles, comprising at least one compound selected from the group consisting of hydroxides of aluminum, oxides of aluminum, hydroxides of silicon and oxides of silicon in an amount of 0.01 to 50% by weight, calculated as Al or $SiO_2$, based on the total weight of the magnetic iron oxide particles;
  a coating layer formed on the surface of the magnetic iron oxide particle, comprising at least one organosilicon compound selected from the group consisting of:
    (1) organosilane compounds obtained from an alkoxysilane compounds, and
    (2) polysiloxanes or modified polysiloxanes; and a carbon black coat formed on at least a part of the coating layer comprising the organosilicon compound, in an amount of 26 to 55 parts by weight based on 100 parts by weight of the magnetic iron oxide particles.

In a third aspect of the present invention, there are provided black magnetic composite particles for a black magnetic toner, comprising:

magnetic iron oxide particles having an average particle diameter of 0.055 to 0.95 μm;
a coating layer formed on the surface of the magnetic iron oxide particle, comprising at least one organosilicon compound selected from the group consisting of:
  (1) organosilane compounds obtained from an alkoxysilane compounds, and
  (2) polysiloxanes or modified polysiloxanes; and a carbon black coat formed on at least a part of the coating layer comprising the organosilicon compound, in an amount of 26 to 55 parts by weight based on 100 parts by weight of the magnetic iron oxide particles.

In a fourth aspect of the present invention, there are provided black magnetic composite particles for a black magnetic toner, comprising:

magnetic iron oxide particles having an average particle diameter of 0.055 to 0.95 μm;
a coat formed on at least a part of the surface of the magnetic iron oxide particles, comprising at least one compound selected from the group consisting of hydroxides of aluminum, oxides of aluminum, hydroxides of silicon and oxides of silicon in an amount of 0.01 to 50% by weight, calculated as Al or $SiO_2$, based on the total weight of the magnetic iron oxide particles;
a coating layer formed on the surface of the magnetic iron oxide particle, comprising at least one organosilicon compound selected from the group consisting of:

(1) organosilane compounds obtained from an alkoxysilane compounds, and (2) polysiloxanes or modified polysiloxanes; and a carbon black coat formed on at least a part of the coating layer comprising the organosilicon compound, in an amount of 26 to 55 parts by weight based on 100 parts by weight of the magnetic iron oxide particles.

In a fifth aspect of the present invention, there is provided a process for producing black magnetic composite particles defined in the third aspect, which process comprises:

mixing as core particles magnetic iron oxide particles having an average particle size of 0.055 to 0.95 µm together with at least one compound selected from the group consisting of:

(1) alkoxysilane compounds, and (2) polysiloxanes or modified polysiloxanes, by using an apparatus capable of applying a shear force to the particles, thereby coating the surface of the magnetic iron oxide particle with the said compounds;

mixing the obtained magnetic iron oxide particles coated with the said compounds and carbon black fine particles having an average particle size of 0.002 to 0.05 µm in an amount of 1 to 25 parts by weight based on 100 parts by weight of the core particles by using an apparatus capable of applying a shear force to the particles, thereby forming a carbon black coat on the surface of the coating layer comprising the said compounds;

mixing the carbon black-coated magnetic iron oxide particles with dimethylpolysiloxanes in an amount of 0.1 to 5 parts by weight based on 100 parts by weight of the core particles by using an apparatus capable of applying a shear force to the particles; and mixing the obtained magnetic iron oxide particles coated with dimethyl polysiloxanes and carbon black fine particles having an average particle size of 0.002 to 0.05 µm in an amount of 1 to 30 parts by weight based on 100 parts by weight of the core particles by using an apparatus capable of applying a shear force to the particles, thereby further forming a carbon black coat through the dimethylpolysiloxanes.

DETAILED DESCRIPTION OF THE INVENTION

The present invention is now described in detail below.

First, the black magnetic composite particles according to the present invention are described.

The black magnetic composite particles according to the present invention, comprise magnetic iron oxide particles as core particles; a coating layer comprising organosilicon compound, formed on the surface of each magnetic iron oxide particle; and a carbon black coat formed in a large amount, and have an average major axial diameter of 0.06 to 1.0 µm.

As the magnetic iron oxide particles used as core particles in the present invention, there may be exemplified magnetite particles ($FeO_x \cdot Fe_2O_3$; $0<X\leq 1$), maghemite particles ($\gamma$-$Fe_2O_3$) or a mixture of these particles. In the consideration of the blackness of the obtained black magnetic composite particles, the magnetite particles are preferred.

As the magnetic iron oxide particles as core particles, from the viewpoint of a particle shape thereof, there may be exemplified isotropic particles having a sphericity (ratio of an average particle length to an average particle breadth; hereinafter referred to merely as "sphericity") of usually not less than 1.0 and less than 2.0, such as spherical particles, granular particles or polyhedral particles, e.g., hexahedral particles or octahedral particles, or anisotropic particles having an aspect ratio (ratio of an average major axial diameter to an average minor axial diameter; hereinafter referred to merely as "aspect ratio") of not less than 2:1, such as acicular particles, spindle-shaped particles or rice ball-shaped particles. In the consideration of the fluidity of the obtained black magnetic composite particles, the magnetic iron oxide particles having an isotropic shape are preferred. Among them, the spherical particles are more preferred.

In the case of the isotropic magnetic iron oxide particles, the average particle size (diameter) thereof is 0.055 to 0.95 µm, preferably 0.065 to 0.75 µm, more preferably 0.065 to 0.45 µm. The sphericity thereof is usually not less than 1.0:1 and less than 2.0:1, preferably 1.0:1 to 1.8:1, and in case where the shape of the magnetic iron oxide particles is spherical, the sphericity thereof is preferably 1.0:1 to 1.4:1, more preferably 1.0:1 to 1.3:1.

In the case of the anisotropic magnetic iron oxide particles, the average major axial diameter thereof is 0.055 to 0.95 µm, preferably 0.065 to 0.75 µm, more preferably 0.065 to 0.45 µm, and the aspect ratio thereof is 2:1 to 20:1, preferably 2:1 to 18:1, more preferably 2:1 to 15:1.

When the average particle size of the magnetic iron oxide particles is more than 0.95 µm, the obtained black magnetic composite particles are coarse particles and are deteriorated in tinting strength. On the other hand, when the average particle size is less than 0.055 µm, the intermolecular force between the particles is increased due to the reduction in particle size (fine particle), so that agglomeration of the particles tends to be caused. As a result, it becomes difficult to uniformly coat the surfaces of the magnetic iron oxide particles with the organosilicon compounds, and uniformly form the carbon black coat on the surface of the coating layer comprising the organosilicon compounds.

Further, in the case where the upper limit of the aspect ratio of the anisotropic magnetic iron oxide particles exceeds 20:1, the particles tend to be entangled with each other, and it also becomes difficult to uniformly coat the surfaces of the magnetic iron oxide particles with the organosilicon compounds, and uniformly form the carbon black coat on the surface of the coating layer composed of the organosilicon compounds.

As to the particle size distribution of the magnetic iron oxide particles, the geometrical standard deviation value thereof is preferably not more than 2.0, more preferably not more than 1.8, still more preferably not more than 1.6. When the geometrical standard deviation value thereof is more than 2.0, coarse particles are contained therein, so that the particles are inhibited from being uniformly dispersed. As a result, it also becomes difficult to uniformly coat the surfaces of the magnetic iron oxide particles with the organosilicon compounds, and uniformly form the carbon black coat on the surface of the coating layer composed of the organosilicon compounds. The lower limit of the geometrical standard deviation value is 1.01. It is industrially difficult to obtain particles having a geometrical standard deviation value of less than 1.01.

The BET specific surface area of the magnetic iron oxide particles thereof is not less than 0.5 $m^2/g$. When the BET specific surface area is less than 0.5 $m^2/g$, the magnetic iron oxide particles may become coarse particles, or the sintering between the particles may be caused, so that the obtained black magnetic composite particles also may become coarse particles and tend to be deteriorated in tinting strength. In the consideration of the tinting strength of the obtained black magnetic composite particles, the BET specific surface area of the magnetic iron oxide particles is preferably not less than 1.0 m²/g, more preferably 1.5 m²/g. Further, in the consideration of uniformly coating the surfaces of the magnetic iron oxide particles with the organosilicon compounds, and uniformly forming the carbon black coat on the coating layer composed of the organosilicon compounds, the upper limit of the BET specific surface area of the magnetic iron oxide particles, is usually 95 m²/g, preferably 90 m²/g, more preferably 85 m²/g.

As to the fluidity of the magnetic iron oxide particles, the fluidity index thereof is about 25 to about 43. Among the magnetic iron oxide particles having various shapes, the spherical particles are excellent in fluidity, for example, the fluidity index thereof is about 30 to about 43.

As to the blackness of the magnetic iron oxide particles, in the case of the magnetite particles, the lower limit thereof is usually 18.0 when represented by $L^*$ value, and the upper limit thereof is usually 26.0, preferably 25.0 when represented by $L^*$ value. In the case of maghemite particles, the lower limit thereof is usually more than 18.0 when represented by $L^*$ value, and the upper limit thereof is usually 34.0, preferably 32.0 when represented by $L^*$ value. When the $L^*$ value exceeds the above-mentioned upper limit, the lightness of the particles is increased, so that it is difficult to obtain black magnetic composite particles having a sufficient blackness.

As to the magnetic properties of the magnetic iron oxide particles, the coercive force value thereof is usually 0.8 to 31.8 kA/m (10 to 400 Oe), preferably 1.6 to 30.2 kA/m (20 to 380 Oe); the saturation magnetization value in a magnetic field of kA/m (10 kOe) is usually 50 to 91 Am²/kg (50 to 91 emu/g), preferably 60 to 90 Am²/kg (60 to 90 emu/g); and the residual magnetization value in a magnetic field of 795.8 kA/m (10 kOe) is usually 1 to 35 Am²/kg (1 to 35 emu/g), preferably 3 to 30 Am²/kg (3 to 30 emu/g).

As the core particles, there may be used magnetic iron oxide particles wherein at least a part of magnetic iron oxide particles is preliminarily coated with at least one compound selected from the group consisting of hydroxide of aluminum, oxides of aluminum, hydroxides of silicon and oxides of silicon (hereinafter referred to as "hydroxides and/or oxides of aluminum and/or silicon") In this case, the dispersibility of the obtained composite particles in a vehicle may become improved as compared to those having no undercoat composed of hydroxides and/or oxides of aluminum and/or silicon, because the percentage of desorption of carbon black from the non-magnetic acicular black iron-based composite particles is lessened.

The amount of the hydroxides and/or oxides of aluminum and/or silicon coat is 0.01 to 50% by weight calculated as Al, $SiO_2$ or a sum of Al and $SiO_2$, based on the weight of the magnetic iron oxide particles as the core particles.

When the amount of the hydroxides and/or oxides of aluminum and/or silicon coat is less than 0.01% by weight; the improvement of the dispersibility of the obtained black magnetic composite particles in a vehicle cannot be achieved because of failing to achieve the improvement of lessening the percentage of desorption of carbon black therefrom. On the other hand, when the amount of the hydroxides and/or oxides of aluminum and/or silicon coat is more than 50% by weight, the obtained black magnetic composite particles can exhibit a good dispersibility in a vehicle by the improvement of lessening the percentage of desorption of carbon black therefrom, but the coating effect is saturated and, therefore, it is meaningless to add such an excess amount of the hydroxides and/or oxides of aluminum and/or silicon coat.

The black magnetic composite particles using as core particles the magnetic iron oxide particles having the coat composed of the hydroxides and/or oxides of aluminum and/or silicon may be substantially identical in a particle size, a geometrical standard deviation, a BET specific surface area, a blackness ($L^*$ value), a fluidity and a magnetic property, to those having no hydroxides and/or oxides of aluminum and/or silicon coat.

The particle shape and particle size of the black magnetic composite particles according to the present invention are considerably varied depending upon those of the magnetic iron oxide particles as core particles. The black magnetic composite particles have a similar particle shape to that of the magnetic iron oxide particle as core particle, and a slightly larger particle size than that of the magnetic iron oxide particles as core particles.

More specifically, when the isotropic magnetic iron oxide particles are used as core particles, the obtained black magnetic composite particles according to the present invention, have an average particle size of usually 0.06 to 1.0 μm, preferably 0.07 to 0.8 μm, more preferably 0.07 to 0.5 μm and a sphericity of usually not less than 1.0:1 and less than 2.0:1, preferably 1.0:1 to 1.8:1, and in case where the shape of the magnetic iron oxide particles is spherical, the sphericity thereof is preferably 1.0:1 to 1.4:1, more preferably 1.0:1 to 1.3:1.

When the anisotropic magnetic iron oxide particles are used as core particles, the obtained black magnetic composite particles according to the present invention, have an average particle size of usually 0.06 to 1.0 μm, preferably 0.07 to 0.8 μm, more preferably 0.07 to 0.5 μm and an aspect ratio of usually 2:1 to 20:1, preferably 2.5:1 to 18:1, more preferably 2:1 to 15:1.

When the average particle size of the black magnetic composite particles is more than 1.0 μm, the obtained black magnetic composite particles may be coarse particles, and deteriorated in tinting strength. On the other hand, when the average particle size thereof is less than 0.06 μm, the black magnetic composite particles may tend to be agglomerated by the increase of intermolecular force due to the reduction in particle size, thereby deteriorating the dispersibility in a binder resin upon production of the magnetic toner.

When the aspect ratio is more than 20:1, the black magnetic composite particles may be entangled with each other in the binder resin, so that the dispersibility in binder resin may tend to be deteriorated.

The geometrical standard deviation value of the black magnetic composite particles according to the present invention is preferably not more than 2.0, more preferably not more than 1.8, still more preferably not more than 1.6. The lower limit of the geometrical standard deviation value thereof is preferably 1.01. When the geometrical standard deviation value thereof is more than 2.0, the tinting strength of the black magnetic composite particles may be likely to be deteriorated due to the existence of coarse particles therein. It is industrially difficult to obtain such particles having a geometrical standard deviation of less than 1.01.

The BET specific surface area of the black magnetic composite particles according to the present invention, is usually 1.0 to 100 m²/g, preferably 1.5 to 95 m²/g, more preferably 2.0 to 90 m²/g. When the BET specific surface area thereof is less than 1.0 m²/g, the obtained black magnetic composite particles may be coarse, and the sintering between the black magnetic composite particles may be caused, thereby deteriorating the tinting strength. On the other hand, when the BET specific surface area is more than 100 m²/g, the black magnetic composite particles may tend to be agglomerated together by the increase in intermolecular force due to the reduction in particle size, thereby deteriorating the dispersibility in a binder resin upon production of the magnetic toner.

As to the fluidity of the black magnetic composite particles according to the present invention, the fluidity index thereof is preferably 48 to 90, more preferably 49 to 90, still more preferably 50 to 90. When the fluidity index thereof is less than 48, the fluidity of the black magnetic composite particles may become insufficient, thereby failing to improve the fluidity of the finally obtained magnetic toner. Further, in the production process of the magnetic toner, there may tend to be caused defects such as clogging of hopper, etc., thereby deteriorating the handling property or workability.

As to the blackness of the black magnetic composite particles according to the present invention, in the case magnetite particles are used as core particles, the upper limit of the blackness of the black magnetic composite particles is usually 19.5, preferably 18.8, more preferably 17.8 when represented by L* value. In the case maghemite particles are used as core particles, the upper limit of the blackness of the black magnetic composite particles is usually 19.5, preferably 19.0, more preferably 18.8 when represented by L* value. When the L* value thereof is more than 19.5, the lightness of the obtained black magnetic composite particles may become high, so that the black magnetic composite particles having a sufficient blackness may not be obtained. The lower limit of the blackness thereof is 15 when represented by L* value.

The dispersibility in binder resin of the black magnetic composite particles according to the present invention, is preferably 4th or 5th rank, more preferably 5th rank when evaluated by the method described hereinafter.

The percentage of desorption of carbon black from the black magnetic composite particles according to the present invention, is preferably not more than 20%, more preferably not more than 10%. When the desorption percentage of the carbon black is more than 20%, the desorbed carbon black may tend to inhibit the black magnetic composite particles from being uniformly dispersed in the binder resin upon production of the magnetic toner.

The magnetic properties of the black magnetic composite particles according to the present invention, can be controlled by appropriately selecting kind and particle shape of the magnetic iron oxide particles as core particles. Similarly to magnetic properties of magnetic particles ordinarily used for the production of magnetic toner, the coercive force of the black magnetic composite particles according to the present invention, is usually 0.8 to 31.8 kA/m (10 to 400 Oe), preferably 1.6 to 30.2 kA/m (20 to 380 Oe); the saturation magnetization in a magnetic field of 795.8 kA/m (10 kOe) is usually 50 to 91 Am²/kg (50 to 91 emu/g), preferably 60 to 90 Am²/kg (60 to 90 emu/g); and the residual magnetization in a magnetic field of 795.8 kA/m (10 kOe) is usually 1 to 35 Am²/kg (1 to 35 emu/g), preferably 3 to 30 Am²/kg (3 to 30 emu/g).

The coating layer formed on the surfaces of the core particles comprises at least one organosilicon compound selected from the group consisting of (1) organosilane compounds obtainable from alkoxysilane compounds; and (2) polysiloxanes, or (2') modified polysiloxanes selected from the group consisting of (A) polysiloxanes modified with at least one compound selected from the group consisting of polyethers, polyesters and epoxy compounds (hereinafter referred to merely as "modified polysiloxanes"), and (B) polysiloxanes whose molecular terminal is modified with at least one group selected from the group consisting of carboxylic acid groups, alcohol groups and a hydroxyl group (hereinafter referred to merely as "terminal-modified polysiloxanes").

The organosilane compounds (1) may be produced by drying or heat-treating alkoxysilane compounds represented by the formula (I):

wherein R¹ is $C_6H_5-$, $(CH_3)_2CHCH_2-$ or $n-C_bH_{2b+1}-$ (wherein b is an integer of 1 to 18); X is $CH_3O-$ or $C_2H_5O-$; and a is an integer of 0 to 3.

The drying or heat-treatment of the alkoxysilane compounds may be conducted, for example, at a temperature of usually 40 to 200° C., preferably 60 to 150° C. for usually 10 minutes to 12 hours, preferably 30 minutes to 3 hours.

Specific examples of the alkoxysilane compounds may include methyltriethoxysilane, dimethyldiethoxysilane, phenyltriethyoxysilane, diphenyldiethoxysilane, methyltrimethoxysilane, dimethyldimethoxysilane, phenyltrimethoxysilane, diphenyldimethoxysilane, isobutyltrimethoxysilane, decyltrimethoxysilane or the like. Among these alkoxysilane compounds, in view of the desorption percentage and the adhering effect of carbon black, methyltriethoxysilane, phenyltriethyoxysilane, methyltrimethoxysilane, dimethyldimethoxysilane and isobutyltrimethoxysilane are preferred, and methyltriethoxysilane and methyltrimethoxysilane are more preferred.

As the polysiloxanes (2), there may be used those compounds represented by the formula (II):

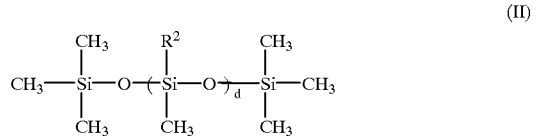

wherein R² is H— or $CH_3-$, and d is an integer of 15 to 450.

Among these polysiloxanes, in view of the desorption percentage and the adhering effect of carbon black, polysiloxanes having methyl hydrogen siloxane units are preferred.

As the modified polysiloxanes (2'-A), there may be used:
(a1) polysiloxanes modified with polyethers represented by the formula (III):

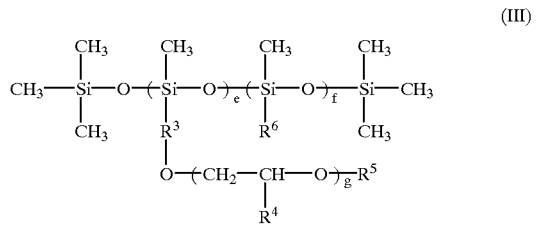

wherein R³ is $-(-CH_2-)_h-$; R⁴ is $-(-CH_2-)_i-CH_3$; R⁵ is —OH, —COOH, —CH=CH₂, —C(CH₃)=CH₂ or $-(-CH_2-)_j-CH_3$; R⁶ is $-(-CH_2-)_k-CH_3$; g and h are an integer of 1 to 15; i, j and k are an integer of 0 to 15; e is an integer of 1 to 50; and f is an integer of 1 to 300;

(a2) polysiloxanes modified with polyesters represented by the formula (IV):

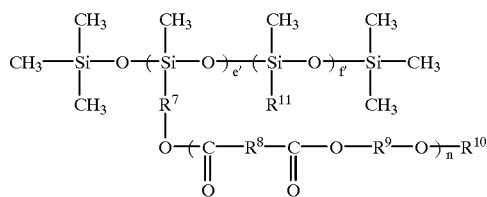

wherein $R^7$, $R^8$ and $R^9$ are $-(-CH_2-)_q-$ and may be the same or different; $R^{10}$ is $-OH$, $-COOH$, $-CH=CH_2$, $-C(CH_3)=CH_2$ or $-(-CH_2-)_r-CH_3$; $R^{11}$ is $-(-CH_2-)_s-CH_3$; n and q are an integer of 1 to 15; r and s are an integer of 0 to 15; e' is an integer of 1 to 50; and f' is an integer of 1 to 300;

(a3) polysiloxanes modified with epoxy compounds represented by the formula (V):

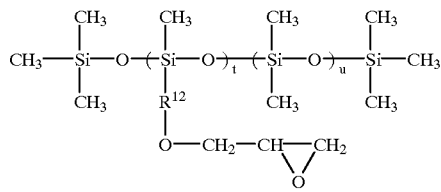

wherein $R^{12}$ is $-(-CH_2-)_v-$; v is an integer of 1 to 15; t is an integer of 1 to 50; and u is an integer of 1 to 300; or a mixture thereof.

Among these modified polysiloxanes (2'-A), in view of the desorption percentage and the adhering effect of carbon black, the polysiloxanes modified with the polyethers represented by the formula (III), are preferred.

As the terminal-modified polysiloxanes (2'-B), there may be used those represented by the formula (VI):

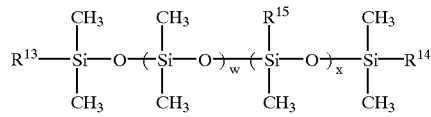

wherein $R^{13}$ and $R^{14}$ are $-OH$, $R^{16}OH$ or $R^{17}COOH$ and may be the same or different; $R^{15}$ is $-CH_3$ or $-C_6H_5$; $R^{16}$ and $R^{17}$ are $-(-CH_2-)_y-$; y is an integer of 1 to 15; w is an integer of 1 to 200; and x is an integer of 0 to 100.

Among these terminal-modified polysiloxanes, in view of the desorption percentage and the adhering effect of carbon black, the polysiloxanes whose terminals are modified with carboxylic acid groups are preferred.

The amount of the coating layer composed of the organosilicon compounds is usually 0.02 to 5.0% by weight, preferably 0.03 to 4.0% by weight, more preferably 0.05 to 3.0% by weight (calculated as Si) based on the weight of the magnetic iron oxide particles coated with the organosilicon compounds.

When amount of the coating layer composed of the organosilicon compounds is less than 0.02% by weight, it becomes difficult to adhere the carbon black on the surfaces of the magnetic iron oxide particles. On the other hand, in case where the coating amount of the organosilicon compounds is more than 5.0% by weight, since the carbon black coat can be sufficiently formed on the surface of the coating layer composed of the organosilicon compounds, it is meaingless to coat an excess amount of the organosilicon compounds.

A carbon black coat is formed on at least a part of the surface of coating layer composed of the organosilicon compounds, and is composed of at least two carbon black layers integrally adhered with each other through an adhesive. If required, 3 or more carbon black layers are integrally adhered with each other through an adhesive to form the carbon black coat.

The amount of the carbon black coat is 26 to 55 parts by weight based on 100 parts by weight of the magnetic iron oxide particles as core particles.

When the amount of the carbon black coat formed is less than 26 part by weight, it becomes difficult to obtain black magnetic composite particles having a sufficient fluidity and blackness. On the other hand, when the amount of the carbon black coat formed is more than 55 parts by weight, the carbon black tend to be desorbed from the coating layer composed of the organosilicon compound. As a result, the obtained black magnetic composite particles tend to be deteriorated in dispersibility in a binder resin upon the production of magnetic toner.

The thickness of carbon black coat formed is preferably not more than 0.06 $\mu$m, more preferably not more than 0.05 $\mu$m, still more preferably not more than 0.04 $\mu$m. The lower limit thereof is more preferably 0.0001 $\mu$m.

In the black magnetic composite particles according to the present invention, at least a part of the surface of the magnetic iron oxide particles as core particle may be preliminarily coated with hydroxides and/or oxides of aluminum and/or silicon. In this case, the obtained black magnetic composite particles can show a higher dispersibility in a binder resin as compared to in the case where the magnetic iron oxide particles are uncoated with hydroxides and/or oxides of aluminum and/or silicon, because of achieving the improvement of lessening the percentage of desorption of carbon black therefrom.

By coating the magnetic iron oxide particle with the hydroxides and/or oxides of aluminum and/or silicon, the percentage of desorption of carbon black from the obtained black magnetic composite particles of the present invention is preferably not more than 10%, more preferably not more than 5%.

Next, the black magnetic toner according to the present invention is described.

The black magnetic toner according to the present invention comprises the black magnetic composite particles, and a binder resin. The black magnetic toner may further contain a mold release agent, a colorant, a charge-controlling agent and other additives, if necessary.

The black magnetic toner according to the present invention has an average particle size of usually 3 to 15 $\mu$m, preferably 5 to 12 $\mu$m.

The amount of the binder resin used in the black magnetic toner is usually 50 to 900 parts by weight, preferably 50 to 400 parts by weight based on 100 parts by weight of the black magnetic composite particles.

As the binder resins, there may be used vinyl-based polymers, i.e., homopolymers or copolymers of vinyl-based monomers such as styrene, alkyl acrylates and alkyl methacrylates. As the styrene monomers, there may be exemplified styrene and substituted styrenes. As the alkyl acrylate monomers, there may be exemplified acrylic acid, methyl acrylate, ethyl acrylate, butyl acrylate or the like.

It is preferred that the above copolymers contain styrene-based components in an amount of usually 50 to 95% by weight.

In the binder resin used in the present invention, the above-mentioned vinyl-based polymers may be used in combination with polyester-based resins, epoxy-based resins, polyurethane-based resins or the like, if necessary.

As to the fluidity of the black magnetic toner according to the present invention, the fluidity index is usually 78 to 100, preferably 79 to 100, more preferably 80 to 100. When the fluidity index is less than 78, the black magnetic toner may not show a sufficient fluidity.

The blackness of the black magnetic toner according to the present invention is usually not more than 19.0, preferably not more than 18.8, more preferably not more than 18.5 when represented by $L^*$ value. When the blackness thereof is more than 19.0, the lightness of the black magnetic toner may be increased, resulting in insufficient blackness. The lower limit of the blackness of the black magnetic toner is usually about 15 when represented by $L^*$ value.

The volume resistivity of the black magnetic toner according to the present invention, is usually not less than $1.0 \times 10^{13}$ Ω·cm, preferably not less than $3.0 \times 10^{13}$ Ω·cm, more preferably not less than $5.0 \times 10^{13}$ Ω·cm. When the volume resistivity is less than $1.0 \times 10^{13}$ Ω·cm, the charge amount of the black magnetic toner tends to vary depending upon environmental conditions in which the toner is used, resulting in unstable properties of the black magnetic toner. The upper limit of the volume resistivity is $1.0 \times 10^{17}$ Ω·cm.

As to the magnetic properties of the black magnetic toner according to the present invention, the coercive force thereof is usually 0.8 to 31.8 kA/m (10 to 400 Oe), preferably 1.6 to 30.2 kA/m (20 to 380 Oe); the saturation magnetization value in a magnetic field of 795.8 kA/m (10 kOe) is usually 10 to 85 $Am^2$/kg (10 to 85 emu/g), preferably 20 to 80 $Am^2$/kg (20 to 80 emu/g); the residual magnetization in a magnetic field of 795.8 kA/m (10 kOe) is usually 1 to 20 $Am^2$/kg (1 to 20 emu/g), preferably $Am^2$/kg (2 to 15 emu/g); the saturation magnetization in a magnetic field of 79.6 kA/m (1 kOe) is usually 7.5 to 65 $Am^2$/kg (7.5 to 65 emu/g), preferably 10 to 60 $Am^2$/kg (10 to 60 emu/g); and the residual magnetization in a magnetic field of 79.6 kA/m (1 kOe) is usually 0.5 to 15 $Am^2$/kg (0.5 to 15 emu/g), preferably 1.0 to 13 $Am^2$/kg (1.0 to 13 emu/g).

Next a process for producing the black magnetic composite particles according to the present invention is described.

Among the isotropic magnetite particles which are magnetic iron oxide particles, (1) octahedral magnetite particles can be produced by passing an oxygen-containing gas through a suspension containing ferrous hydroxide colloid having a pH value of not less than 10, which is obtained by reacting an aqueous ferrous salt solution with an aqueous alkali solution having a concentration of not less than one equivalent based on $Fe^{2+}$ in the aqueous ferrous salt solution, thereby precipitating magnetite particles, and then subjecting the obtained magnetite particles to filtering, washing with water and drying (Japanese Patent Publication (KOKOKU) No. 44-668(1969); (2) hexahedral magnetite particles can be produced by passing an oxygen-containing gas through a suspension containing ferrous hydroxide colloid having a pH value of 6.0 to 7.5, which is obtained by reacting an aqueous ferrous salt solution with an aqueous alkali solution having a concentration of not more than one equivalent based on $Fe^{2+}$ in the aqueous ferrous salt solution to produce magnetite core particles, further passing an oxygen-containing gas through the obtained aqueous ferrous salt reaction solution containing the magnetite core particles and the ferrous hydroxide colloid, at a pH value of 8.0 to 9.5, to precipitate magnetite particles, and then subjecting the precipitated magnetite particles to filtering, washing with water and drying (Japanese Patent Application Laid-Open (KOKAI) No. 3-201509(1991); (3) spherical magnetite particles can be produced by passing an oxygen-containing gas through a suspension containing ferrous hydroxide colloid having a pH value of 6.0 to 7.5, which is obtained by reacting an aqueous ferrous salt solution with an aqueous alkali solution having a concentration of not more than one equivalent based on $Fe^{2+}$ in the aqueous ferrous salt solution to produce magnetite core particles, adding alkali hydroxide in an amount of not less than equivalent based on the remaining $Fe^{2+}$ to adjust the pH value of the suspension to not less than 10, heat-oxidizing the resultant suspension to precipitate magnetite particles, and then subjecting the precipitated magnetite particles to filtering, washing with water and drying (Japanese Patent Publication (KOKOKU) No. 62-51208(1987).

The isotropic maghemite particles can be obtained by heating the above-mentioned isotropic magnetite particles in air at 300 to 600° C.

The anisotropic magnetite particles can be produced by passing an oxygen-containing gas through a suspension containing either ferrous hydroxide colloid, iron carbonate, or an iron-containing precipitate obtained by reacting an aqueous ferrous salt solution with alkali hydroxide and/or alkali carbonate, while appropriately controlling the pH value and temperature of the suspension, to produce acicular, spindle-shaped or rice ball-shaped goethite particles, subjecting the obtained goethite particles to filtering, washing with water and drying, and then reducing the goethite particles in a heat-reducing gas at 300 to 800° C.

The anisotropic maghemite particles can be produced by heat-oxidizing the above-mentioned anisotropic magnetite particles in an oxygen-containing gas at 300 to 600° C.

The coating of the magnetic iron oxide particles with the alkoxysilane compounds, the polysiloxanes, the modified polysiloxanes or the terminal-modified polysiloxanes, may be conducted (i) by mechanically mixing and stirring the magnetic iron oxide particles together with the alkoxysilane compounds, the polysiloxanes, the modified polysiloxanes or the terminal-modified polysiloxanes; or (ii) by mechanically mixing and stirring both the components together while spraying the alkoxysilane compounds, the polysiloxanes, the modified polysiloxanes or the terminal-modified polysiloxanes onto the magnetic iron oxide particles. In these cases, substantially whole amount of the alkoxysilane compounds, the polysiloxanes, the modified polysiloxanes or the terminal-modified polysiloxanes added can be applied onto the surfaces of the magnetic iron oxide particles.

In order to uniformly coat the surfaces of the magnetic iron oxide particles with the alkoxysilane compounds, the polysiloxanes, the modified polysiloxanes or the terminal-modified polysiloxanes, it is preferred that the magnetic iron oxide particles are preliminarily diaggregated by using a pulverizer.

As apparatuses used for (a) mixing and stirring the core particles with alkoxysilane compounds, the polysiloxanes, the modified polysiloxanes or the terminal-modified polysiloxanes; (b) mixing and stirring the carbon black fine particles with the particles surface-coated with alkoxysilane compounds, the polysiloxanes, the modified polysiloxanes or the terminal-modified polysiloxanes; (c) mixing and stirring the adhesive with the particles having a first carbon black coat formed onto the surface-coating composed of alkoxysilane compounds, the polysiloxanes, the modified polysiloxanes or the terminal-modified polysiloxanes (hereinafter referred to as "composite particles"); and (d) mixing and stirring the carbon black fine particles with the composite particles coated with the adhesive, there may be preferably used apparatus capable of applying a shearing force to a layer of the particles to be treated, more preferably those capable of conducting shearing, spatula-stroking and compression at the same time, for example, wheel-type kneader, ball-type kneader, blade-type kneader, roll-type kneader or the like. Among these apparatuses, the wheel-type kneader is more effective for the practice of the present invention.

Specific examples of the wheel-type kneaders may include an edge runner (equal to a mix muller, a Simpson mill or a sand mill), a multi-mull, a Stotz mill, a wet pan mill, a Conner mill, a ring muller, or the like. Among them, an edge runner, a multi-mull, a Stotz mill, a wet pan mill and a ring muller are preferred, and an edge runner is more preferred.

Specific examples of the ball-type kneaders may include a vibrating mill or the like. Specific examples of the blade-type kneaders may include a Henschel mixer, a planetary mixer, a Nawter mixer or the like. Specific examples of the roll-type kneaders may include an extruder or the like.

In order to coat the surfaces of the core particles with the alkoxysilane compounds, the polysiloxanes, the modified polysiloxanes or the terminal-modified polysiloxanes as uniformly as possible, the conditions of the above mixing or stirring treatment may be appropriately controlled such that the linear load is usually 19.6 to 1960 N/cm (2 to 200 Kg/cm), preferably 98 to 1470 N/cm (10 to 150 kg/cm), more preferably 147 to 980 N/cm (15 to 100 kg/cm); and the treating time is usually 5 to 120 minutes, preferably 10 to 90 minutes. It is preferred to appropriately adjust the stirring speed in the range of usually 2 to 2,000 rpm, preferably 5 to 1,000 rpm, more preferably 10 to 800 rpm.

The amount of the alkoxysilane compounds, the polysiloxanes, the modified polysiloxanes or the terminal-modified polysiloxanes added, is preferably 0.15 to 45 parts by weight based on 100 parts by weight of the magnetic iron oxide particles. When the amount of the alkoxysilane compounds, the polysiloxanes, the modified polysiloxanes or the terminal-modified polysiloxanes added is less than 0.15 part by weight, it may become difficult to form the carbon black coat on the coating layer.

On the other hand, when the amount of the alkoxysilane compounds, the polysiloxanes, the modified polysiloxanes or the terminal-modified polysiloxanes added is more than 45 parts by weight, a sufficient amount of the carbon black coat can be formed on the surface of the coating, and therefore, it is meaningless to add such an excess amount of the alkoxysilane compounds, the polysiloxanes, the modified polysiloxanes or the terminal-modified polysiloxanes.

Meanwhile, a part of the alkoxysilanes coated on the surfaces of the core particles may be converted into the organosilane compounds via the coating step thereof. Even in such a case, the subsequent adhesion step with carbon black is not adversely affected.

Next, the carbon black fine particles are added to the magnetic iron oxide particles coated with the polysiloxanes, the modified polysiloxanes or the terminal-modified polysiloxanes, and the resultant mixture is mixed and stirred to form a first carbon black coat on the surfaces of the coating composed of the the polysiloxanes, the modified polysiloxanes or the terminal-modified polysiloxanes added.

In order to form carbon black coat onto the coating layer composed of the alkoxysilane compounds, the polysiloxanes, the modified polysiloxanes or the terminal-modified polysiloxanes as uniformly as possible, the conditions of the above mixing or stirring treatment can be appropriately controlled such that the linear load is usually 2 to 200 Kg/cm, preferably 10 to 150 Kg/cm more preferably 15 to 100 Kg/cm; and the treating time is usually 5 to 120 minutes, preferably 10 to 90 minutes. It is preferred to appropriately adjust the stirring speed in the range of usually 2 to 2,000 rpm, preferably 5 to 1,000 rpm, more preferably 10 to 800 rpm.

The amount of the carbon black fine particles added for forming the first carbon black coat, is usually 1 to 25 parts by weight, preferably 5 to 25 parts by weight based on 100 parts by weight of the magnetic iron oxide particles. When the amount of carbon black fine particles added for forming the first carbon black coat is less than 1 part by weight, the amount of the adhesive capable of adhering onto the first carbon black coat also may become insufficient. As a result, when carbon black fine particles for forming a second carbon black coat are subsequently added such that the total amount of carbon black adhered is not less than 26 parts by weight based on 100 parts by weight of the magnetic iron oxide particles as core particles, the desorption percentage of carbon black is disadvantageously increased, resulting in deteriorated dispersibility in a binder resin upon production of the magnetic toner.

On the contrary, when the amount of carbon black adhered is as large as more than 25 parts by weight, the carbon black tends to be desorbed or fallen-off from the surface of each composite particle. Therefore, the carbon black also tends to be desorbed or fallen-off from the surfaces of the obtained black magnetic composite particles, resulting in deteriorated dispersibility in a binder resin upon production of the magnetic toner.

As the carbon black fine particles used in the present invention, there may be exemplified commercially available carbon blacks such as furnace black, channel black or the like. Specific examples of the commercially available carbon blacks usable in the present invention, may include #3050, #3150, #3250, #3750, #3950, MA100, MA7, #1000, #2400B, #30, MA77, MA8, #650, MA11, #50, #52, #45, #2200B, MA600, etc. (tradename, produced by MITSUBISHI CHEMICAL CORP.), SEAST 9H, SEAST 7H, SEAST 6, SEAST 3H, SEAST 300, SEAST FM, etc. (tradename, produced by TOKAI CARBON CO., LTD.), Raven 1250, Raven 860 ULTRA, Raven 1000, Raven 1190 ULTRA, etc. (tradename, produced by COLOMBIAN CHEMICALS COMPANY), Ketchen black EC, Ketchen black EC600JD, etc. (tradename, produced by KETCHEN BLACK INTERNATIONAL CO., LTD.), BLACK PEARLS-L, BLACK PEARLS 1000, BLACK PEARLS 4630, VULCAN XC72, REGAL 660, REGAL 400, etc. (tradename, produced by CABOTT SPECIALTY CHEMICALS INK CO., LTD.), or the like.

In order to uniformly form the carbon black coat onto the coating composed of the alkoxysilane compounds, the polysiloxanes, the modified polysiloxanes or the terminal-modified polysiloxanes, or the dimethylpolysiloxane coating layer while suppressing the reduction of volume resistivity value of the obtained composite particles, the use of carbon black fine particles having a DBP oil absorption of not more than 150 ml/100 g is preferred. Specific examples of the commercially available carbon blacks usable in the present invention, may include MA100, MA7, #1000, #2400B, #30, MA77, MA8, #650, MA11, #50, #52, #45, #2200B, MA600, etc. (tradename, produced by MITSUBISHI CHEMICAL CORP.), SEAST 9H, SEAST 7H, SEAST 6, SEAST 3H, SEAST 300, etc. (tradename, produced by TOKAI CARBON CO., LTD.), Raven 1250, Raven 860 ULTRA, Raven 1000, Raven 1190 ULTRA, etc. (tradename, produced by COLOMBIAN CHEMICALS COMPANY), BLACK PEARLS-L, BLACK PEARLS 1000, BLACK PEARLS 4630, REGAL 660, REGAL 400, etc. (tradename, produced by CABOTT SPECIALTY CHEMICALS INK CO., LTD.).

The average particle size of the carbon black fine particles used is usually 0.002 to 0.05 μm, preferably 0.002 to 0.035 μm. When the average particle size of the carbon black fine particles used is less than 0.002 μm, the carbon black fine particles used are too fine to be well handled.

On the other hand, when the average particle size thereof is more than 0.05 μm, since the particle size of the carbon black fine particles used is much larger, it is necessary to apply a larger mechanical shear force for forming the uniform carbon black coat on the coating layer composed of the organosilicon compounds, thereby rendering the coating process industrially disadvantageous.

It is preferred that the carbon black fine particles are added little by little and slowly, especially about 5 to 60 minutes.

In order to form the first carbon black coat onto the coating layer composed of the alkoxysilane compounds, the polysiloxanes, the modified polysiloxanes or the terminal-modified polysiloxanes as uniformly as possible, the conditions of the above mixing or stirring treatment can be appropriately controlled such that the linear load is usually 19.6 to 1960 N/cm (2 to 200 Kg/cm), preferably 98 to 1470 N/cm (10 to 150 Kg/cm), more preferably 147 to 980 N/cm (15 to 100 Kg/cm); and the treating time is usually 5 to 120 minutes, preferably 10 to 90 minutes. It is preferred to appropriately adjust the stirring speed in the range of usually 2 to 2,000 rpm, preferably 5 to 1,000 rpm, more preferably 10 to 800 rpm.

Then, a second carbon black coat is formed onto the first carbon black coat through an adhesive such as dimethylpolysiloxanes.

The first and second carbon black coats can be bonded to each other by adhering the carbon black themselves through the adhesive, thereby obtaining a carbon black coat wherein the first and second carbon black coats are integrated. In order to obtain black magnetic composite particles exhibiting excellent fluidity and blackness, in which the two carbon black coats are firmly and uniformly bonded together, dimethylpolysiloxanes represented by the following formula is preferably used as the adhesive.

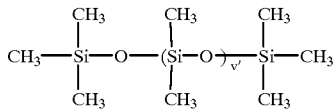

wherein v' is a is an integer of 15 to 450.

The amount of the adhesive added is usually 0.1 to 5.0 parts by weight, preferably 0.2 to 4.0 parts by weight, more preferably 0.3 to 3.0 parts by weight based on 100 parts by weight of the core particles.

When the amount of the adhesive adhered is less than 0.1 part by weight, it may be difficult to sufficiently bond the second carbon black coat onto the first carbon black coat, thereby failing to obtain black magnetic composite particles exhibiting a more excellent fluidity and a more excellent blackness.

When the amount of the adhesive adhered is more than 5.0 part by weight, the carbon black can be adhered thereon in such an amount enough to achieve the more excellent fluidity and blackness of the obtained black magnetic composite particles. However, since the effect is already saturated, it is unnecessary to use such a large amount of the adhesive.

The amount of the adhesive is usually 0.04 to 1.89% by weight, preferably 0.08 to 1.51% by weight, more preferably 0.11 to 1.13% by weight (calculated as Si) based on the weight of the magnetic iron oxide particles.

After the adhesive is added to, and then mixed and stirred with the composite particles on which the first carbon black coat is formed, the carbon black fine particles are added to, and then mixed and stirred with the resultant mixture to form the second carbon black coat onto the first carbon black coat through the adhesive, thereby integrating the carbon black coats. The thus obtained composite particles may be dried and heat-treated, if required.

The mixing and stirring conditions for adhering the adhesive onto the composite particles on which the first carbon black coat is formed, may be appropriately selected such that the adhesive can be uniformly coated onto the first carbon black coat of each composite particle. More specifically, the linear load used for the mixing and stirring is usually 19.6 to 1,960 N/cm (2 to 200 kg/cm), preferably 98 to 1,470 N/cm (10 to 150 kg/cm), more preferably 147 to 980 N/cm (15 to 100 kg/cm); the treating time is 5 to 120 minutes, preferably 10 to 90 minutes; and the stirring speed is usually 2 to 2,000 rpm, preferably 5 to 1,000 rpm, more preferably 10 to 800 rpm.

The amount of the carbon black fine particles added for forming the second carbon black coat is 1 to 30 parts by weight based on 100 parts by weight of the magnetic iron oxide particles. When the amount of the carbon black fine particles added is less than 1 part by weight, the total amount of carbon black adhered becomes insufficient, so that it may be difficult to obtain aimed black magnetic composite particles which are more excellent in fluidity and blackness. On the contrary, when the amount of the carbon black fine particles added is more than 30 part by weight, the carbon black tends to be desorbed or fallen-off from the surfaces of the obtained black magnetic composite particles, resulting in deteriorated dispersibility in a binder resin upon production of the magnetic toner.

The mixing and stirring conditions for forming the second carbon black coat onto the first carbon black coat through the adhesive, may be appropriately selected such that the second carbon black coat can be uniformly coated onto the first carbon black coat through the adhesive. More specifically, the linear load used for the mixing and stirring is usually 19.6 to 1,960 N/cm (2 to 200 kg/cm), preferably 98 to 1,470 N/cm (10 to 150 kg/cm), more preferably 147 to 980 N/cm (15 to 100 kg/cm); the treating time is 5 to 120 minutes, preferably 10 to 90 minutes; and the stirring speed is usually 2 to 2,000 rpm, preferably 5 to 1,000 rpm, more preferably 10 to 800 rpm.

In the case where the alkoxysilane compounds are used as the coating compound, the resultant black magnetic composite particles may be dried or heat-treated, for example, at a temperature of usually 40 to 200° C., preferably 60 to 150° C. for usually 10 minutes to 12 hours, preferably 30 minutes to 3 hours.

At least a part of the surface of the magnetic iron oxide particles as core particles may be coated with at least one compound selected from the group consisting of hydroxides of aluminum, oxides of aluminum, hydroxides of silicon and oxides of silicon, in advance of mixing and stirring with the alkoxysilane compounds, the polysiloxanes, the modified polysiloxanes or the terminal-modified polysiloxanes.

The coat of the hydroxides and/or oxides of aluminum and/or silicon may be conducted by adding an aluminum compound, a silicon compound or both the compounds to a water suspension in which the magnetic iron oxide particles are dispersed, followed by mixing and stirring, and further adjusting the pH value of the suspension, if required, thereby coating the surfaces of the magnetic iron oxide particles with at least one compound selected from the group consisting of hydroxides of aluminum, oxides of aluminum, hydroxides of silicon and oxides of silicon. The thus obtained particles coated with the hydroxides and/or oxides of aluminum and/or silicon are then filtered out, washed with water, dried and pulverized. Further, the particles coated with the hydroxides and/or oxides of aluminum and/or silicon may be subjected to post-treatments such as deaeration treatment and compaction treatment.

As the aluminum compounds, there may be exemplified aluminum salts such as aluminum acetate, aluminum sulfate, aluminum chloride or aluminum nitrate, alkali aluminates such as sodium aluminate or the like.

The amount of the aluminum compound added is 0.01 to 50% by weight (calculated as Al) based on the weight of the magnetic iron oxide particles. When the amount of the aluminum compound added is less than 0.01% by weight., it may be difficult to sufficiently coat the surfaces of the magnetic iron oxide particles with hydroxides and/or oxides of aluminum, which can achieve the improvement of lessening the percentage of desorption of carbon black therefrom, thereby failing to achieve the improvement of the dispersibility in the binder resin upon the production of the magnetic toner. On the other hand, when the amount of the aluminum compound added is more than 50% by weight, the coating effect is saturated and, therefore, it is meaningless to add such an excess amount of the aluminum compound.

As the silicon compounds, there may be exemplified water glass #3, sodium orthosilicate, sodium metasilicate, colloidal silica or the like.

The amount of the silicon compound added is 0.01 to 50% by weight (calculated as $SiO_2$) based on the weight of the magnetic iron oxide particles. When the amount of the silicon compound added is less than 0.01% by weight, it may be difficult to sufficiently coat the surfaces of the magnetic iron oxide particles with hydroxides and/or oxides of silicon, which can achieve the improvement of lessening the percentage of desorption of carbon black therefrom, thereby failing to achieve the improvement of the dispersibility in the binder resin upon the production of the magnetic toner. On the other hand, when the amount of the silicon compound added is more than 50% by weight, the coating effect is saturated and, therefore, it is meaningless to add such an excess amount of the silicon compound.

In the case where both the aluminum and silicon compounds are used in combination for the coating, the total amount of the aluminum and silicon compounds added is preferably 0.01 to 50% by weight (calculated as a sum of Al and $SiO_2$) based on the weight of the magnetic iron oxide particles.

The black magnetic toner according to the present invention may be produced by a known method of mixing and kneading a predetermined amount of a binder resin and a predetermined amount of the black magnetic composite particles together, and then pulverizing the mixed and kneaded material into particles. More specifically, the black magnetic composite particles and the binder resin are intimately mixed together with, if necessary, a mold release agent, a colorant, a charge-controlling agent or other additives by using a mixer. The obtained mixture is then melted and kneaded by a heating kneader so as to render the respective components compatible with each other, thereby dispersing the black magnetic composite particles therein. Successively, the molten mixture is cooled and solidified to obtain a resin-kneaded product. The resin-kneaded product is then pulverized and classified, thereby producing a magnetic toner having an aimed particle size.

As the mixers, there may be used a Henschel mixer, a ball mill or the like. As the heating kneaders, there may be used a roll mill, a kneader, a twin-screw extruder or the like. The pulverization of the resin mixture may be conducted by using pulverizers such as a cutter mill, a jet mill or the like. The classification of the pulverized particles may be conducted by known methods such as air classification, etc., as described in Japanese Patent No. 2683142 or the like.

As the other method of producing the black magnetic toner, there may be exemplified a suspension polymerization method or an emulsion polymerization method. In the suspension polymerization method, polymerizable monomers and the black magnetic composite particles are intimately mixed together with, if necessary, a colorant, a polymerization initiator, a cross-linking agent, a charge-controlling agent or the other additives and then the obtained mixture is dissolved and dispersed together so as to obtain a monomer composition. The obtained monomer composition is added to a water phase containing a suspension stabilizer while stirring, thereby granulating and polymerizing the composition to form magnetic toner particles having an aimed particle size.

In the emulsion polymerization method, the monomers and the black magnetic composite particles are dispersed in water together with, if necessary, a colorant, a polymerization initiator or the like and then the obtained dispersion is polymerized while adding an emulsifier thereto, thereby producing magnetic toner particles having an aimed particle size.

A point of the present invention lies in such a fact that the black magnetic composite particles according to the present invention which are obtained by firmly adhering carbon black onto the surfaces of magnetic iron oxide particles in an amount of 26 to 55 parts by weight based on 100 parts by weight of the magnetic iron oxide particles, are not only more excellent in fluidity and blackness, but also have a less amount of carbon black desorbed or fallen-off from the surface of each particle.

The reason why the black magnetic composite particles of the present invention can exhibit a more excellent fluidity, is considered as follows. In general, the carbon black tends to act as aggregates because of its fineness. In contrast, in the case of the black magnetic composite particles of the present invention, since the carbon black is uniformly and densely adhered and bonded onto the surface of each magnetic iron oxide particle, it is considered that many fine irregularities are formed on the surface of each magnetic iron oxide particle.

The reason why the black magnetic composite particles of the present invention can exhibit a more excellent blackness, is considered as follows. That is, since a uniform carbon black coat having an appropriate thickness is formed by densely adhering and bonding carbon black onto the surface of each magnetic iron oxide particle, the color of the magnetic iron oxide particles is hidden behind the carbon black coat, so that an inherent black color of the carbon black can be effectively exhibited.

The reason why the amount of the carbon black desorbed (or fallen-off) from the surfaces of the black magnetic composite particles according to the present invention, is small, is considered as follows. In the case of the alkoxysilane compounds (1) and the fluoroalkylsilane compounds (3), metalloxane bonds ($\equiv$Si—O—M wherein M represents a metal atom contained in the magnetic iron oxide particles, such as Si, Al, Fe or the like) are formed between the surfaces of the magnetic iron oxide particles and alkoxy groups contained in the organosilicon compounds onto which the carbon black coat is formed, thereby forming a stronger bond between the organosilicon compounds on which the carbon black coat is formed, and the surfaces of the magnetic iron oxide particles. Further, in the case of using the polysiloxanes or modified polysiloxanes, the functional groups in the polysiloxanes or modified polysiloxanes onto which the carbon black coat is formed, are strongly bonded to the surface of the magnetic iron oxide particle.

In accordance with the present invention, due to the less amount of carbon black desorbed or fallen-off from the surface of each black magnetic composite particle, materials present in the system can be well dispersed together without any disturbance by the desorbed carbon black. Further, since irregularities are formed on the surface of each magnetic iron oxide particle by the carbon black adhered and bonded thereonto, the particles are prevented from contacting with each other, resulting in excellent dispersibility in a binder resin upon production of the magnetic toner.

The black magnetic toner according to the present invention obtained by using the above black magnetic composite particles adhered with a large amount of carbon black, can exhibit more excellent fluidity and blackness while maintaining as high a resistivity as not less than $1 \times 10^{13}$ $\Omega \cdot$cm.

The reason why the black magnetic toner of the present invention exhibits a more excellent fluidity, is considered as follows. That is, the black magnetic composite particles obtained by uniformly adhering a large amount of carbon black onto the surface of each magnetic iron oxide particle, are exposed to the surface of the black magnetic toner, thereby forming many fine irregularities thereon.

The reason why the black magnetic toner of the present invention exhibits a more excellent blackness, is considered by the present inventors as follows. That is, the black magnetic composite particles having a more excellent blackness are blended in the black magnetic toner.

The reason why the black magnetic toner of the present invention can maintain a high volume resistivity value nevertheless a large amount of carbon black is adhered onto the surfaces thereof, is considered by the present inventors as follow.

That is, in general, carbon black is present in the form of aggregated particles constituted from parallel-stacked crystallites each having a pseudo-graphite structure. Further, the carbon black fine particles are chemically and physically bonded with each other to form a cluster-like (grape-like cluster) structure. It is known that the larger the cluster-like structure, the higher the electrical conductivity of carbon black becomes. In the case where the carbon black fine particles having such a cluster-like structure are added to and mixed with a binder resin, those exposed to the surface of the magnetic toner also have the cluster-like structure, thereby increasing a conductivity of the magnetic toner. As a result, it is difficult to obtain a magnetic toner having a high volume resistivity value. On the contrary, in the case of the black magnetic composite particles according to the present invention, the carbon black coat is formed onto the surface of each magnetic iron oxide particle without forming the cluster-like structure. Therefore, since the magnetic toner using such black magnetic composite particles are also free from carbon black having the cluster-like structure, thereby maintaining a high volume resistivity value.

The black magnetic composite particles according to the present invention are not only more excellent in fluidity and blackness, but also show an excellent dispersibility in a binder resin due to a less amount of carbon black desorbed or fallen-off from the surface of each particle. Therefore, the black magnetic composite particles of the present invention are suitable as black magnetic particles capable of achieving a high image quality and a high copying speed.

Also, the black magnetic composite particles of the present invention have an excellent dispersibility, i.e., an excellent handling property and are, therefore, industrially advantageous.

The black magnetic toner obtained by using such black magnetic composite particles having more excellent fluidity and blackness, can also exhibit more excellent fluidity and blackness and is, therefore, suitable as black magnetic toner for achieving a high image quality and a high copying speed.

Further, the black magnetic toner of the present invention can maintain a high volume resistivity value nevertheless the use of black magnetic composite particles adhered with a large amount of carbon black. Therefore, the black magnetic toner of the present invention is suitable as high-resistant or insulating magnetic toner.

EXAMPLES

The present invention is described in more detail by Examples and Comparative Examples, but the Examples are only illustrative and, therefore, not intended to limit the scope of the present invention.

Various properties were measured by the following methods.

(1) The average particle size, the average major axial diameter and average minor axial diameter of magnetic iron oxide particles, composite particles, black magnetic composite particles and carbon black fine particles were respectively expressed by the average of values (measured in a predetermined direction) of about 350 particles which were sampled from a micrograph obtained by magnifying an original electron micrograph (×20,000) by four times in each of the longitudinal and transverse directions.

(2) The aspect ratio of the particles was expressed by the ratio of an average major axial diameter to an average minor axial diameter thereof. The sphericity of the particles was expressed by the ratio of an average particle length to an average particle breadth thereof.

(3) The geometrical standard deviation of particle sizes was expressed by values obtained by the following method. That is, the particle sizes (major axial diameters) were measured from the above magnified electron micrograph. The actual particle sizes (major axial diameters) and the number of the particles were calculated from the measured values. On a logarithmic normal probability paper, the particle sizes (major axial diameters) were plotted at regular intervals on the abscissa-axis and the accumulative number (under integration sieve) of particles belonging to each interval of the particle sizes (major axial diameters) were plotted by percentage on the ordinate-axis by a statistical technique.

The particle sizes (major axial diameters) corresponding to the number of particles of 50% and 84.13%, respectively, were read from the graph, and the geometrical standard deviation was calculated from the following formula:

Geometrical standard deviation={particle size (major axial diameters) corresponding to 84.13% under integration sieve}/{particle size (major axial diameters) (geometrical average diameter) corresponding to 50% under integration sieve}

The closer to 1 the geometrical standard deviation value, the more excellent the particle size distribution.

(4) The specific surface area was expressed by the value measured by a BET method.

(5) The amounts of Al and Si which were present within black magnetic composite particles or on surfaces thereof, and the amount of Si contained in organosilicon compounds and the amount of Si contained in dimethylpolysiloxanes used for adhering the carbon black, were measured by a fluorescent X-ray spectroscopy device 3063 M (manufactured by Rigaku Denki Kogyo Co., Ltd.) according to JIS K0119 "General rule of fluorescent X-ray analysis".

(6) The amount of carbon black coat formed on the surface of the magnetic iron oxide particles was measured by "Horiba Metal, Carbon and Sulfur Analyzer EMIA-2200 Model" (manufactured by Horiba Seisakusho Co., Ltd.).

(7) The thickness of carbon black coat formed on the surfaces of the magnetic iron oxide particles is expressed by the value which was obtained by first measuring an average thickness of carbon black coat formed onto the surfaces of the particles on a photograph (×5,000,000) obtained by magnifying (ten times) a micrograph (×500,000) produced at an accelerating voltage of 200 kV using a transmission-type electron microscope (JEM-2010, manufactured by Japan Electron Co., Ltd.), and then calculating an actual thickness of carbon black coat formed from the measured average thickness.

(8) The fluidity of magnetic iron oxide particles, composite particles, black magnetic composite particles and magnetic toner was expressed by a fluidity index which was a sum of indices obtained by converting on the basis of the same reference measured values of an angle of repose, a degree of compaction (%), an angle of spatula and a degree of agglomeration as particle characteristics which were measured by a powder tester (tradename, produced by Hosokawa Micron Co., Ltd.). The closer to 100 the fluidity index, the more excellent the fluidity of the particles.

(9) The blackness of magnetic iron oxide particles, composite particles, black magnetic composite particles and magnetic toner was measured by the following method. That is, 0.5 g of sample particles and 1.5 ml of castor oil were intimately kneaded together by a Hoover's muller to form a paste. 4.5 g of clear lacquer was added to the obtained paste and was intimately kneaded to form a paint. The obtained paint was applied on a cast-coated paper by using a 6-mil (150 μm) applicator to produce a coating film piece (having a film thickness of about 30 μm). The thus obtained coating film piece was measured according to JIS Z 8729 by a multi-light source spectrographic colorimeter MSC-IS-2D (manufactured by Suga Testing Machines Manufacturing Co., Ltd.) to determine an L* value of colorimetric indices thereof. The blackness was expressed by the L* value measured.

Here, the L* value represents a lightness, and the smaller the L* value, the more excellent the blackness.

(10) The desorption percentage of carbon black desorbed from the composite particles and the black magnetic composite particles was measured by the following method. The closer to zero the desorption percentage, the smaller the amount of carbon black desorbed from the surfaces of the composite particles and the black magnetic composite particles.

That is, 3 g of the sample particles and 40 ml of ethanol were placed in a 50-ml precipitation pipe and then were subjected to ultrasonic dispersion for 20 minutes. Thereafter, the obtained dispersion was allowed to stand for 120 minutes, and the carbon black desorbed was separated from the sample particles on the basis of the difference in specific gravity between both the particles. Next, the particles from which the desorbed carbon black was separated, were mixed again with 40 ml of ethanol, and the obtained mixture was further subjected to ultrasonic dispersion for 20 minutes. Thereafter, the obtained dispersion was allowed to stand for 120 minutes, thereby separating the particles and the desorbed carbon black desorbed from each other. The thus obtained particles were dried at 100° C. for one hour, and then the carbon content thereof was measured by the "Horiba Metal, Carbon and Sulfur Analyzer EMIA-2200 Model" (manufactured by Horiba Seisakusho Co., Ltd.). The desorption percentage of the carbon black was calculated according to the following formula:

Desorption percentage of carbon black (%)=$\{(W_a-W_e)/W_a\} \times 100$ wherein $W_a$ represents an amount of carbon black initially formed on the composite particles or the black magnetic composite particles; and We represents an amount of carbon black still adhered on the composite particles or the black magnetic composite particles after desorption test.

(11) The dispersibility in a binder resin of the black magnetic composite particles was evaluated by counting the number of undispersed agglomerated particles on a micrograph (×200) obtained by photographing a sectional area of the obtained black magnetic toner particle using an optical microscope (BH-2, manufactured by Olympus Kogaku Kogyo Co., Ltd.), and classifying the results into the following five ranks. The 5th rank represents the most excellent dispersing condition.

Rank 1: not less than 50 undispersed agglomerated particles per 0.25 mm$^2$ were recognized;

Rank 2: 10 to 49 undispersed agglomerated particles per 0.25 mm$^2$ were recognized;

Rank 3: 5 to 9 undispersed agglomerated particles per 0.25 mm$^2$ were recognized;

Rank 4: 1 to 4 undispersed agglomerated particles per 0.25 mm$^2$ were recognized;

Rank 5: No undispersed agglomerated particles were recognized.

(12) The average particle size of the black magnetic toner was measured by a laser diffraction-type particle size distribution-measuring apparatus (Model HELOSLA/KA, manufactured by Sympatec Corp.).

(13) The volume resistivity of the black magnetic toner was measured by the following method.

That is, first, 0.5 g of a sample toner to be measured was weighted, and press-molded at $1.372 \times 10^7$ Pa (140 Kg/cm$^2$) using a KBr tablet machine (manufactured by Simazu Seisakusho Co., Ltd.), thereby forming a cylindrical test piece.

Next, the thus obtained cylindrical test piece was exposed to an atmosphere maintained at a temperature of 25° C. and a relative humidity of 60% for 12 hours. Thereafter, the cylindrical test piece was set between stainless steel electrodes, and a voltage of 15V was applied between the electrodes using a Wheatstone bridge (TYPE2768, manufactured by Yokogawa-Hokushin Denki Co., Ltd.) to measure a resistance value (Ω).

The cylindrical test piece was measured with respect to an upper surface area A (cm$^2$) and a thickness $t_0$ (cm) thereof.

The measured values were inserted into the following formula, thereby obtaining a volume resistivity X (Ω·cm).

Resistance value (Ω·cm)=$R \times (A/t_0)$

(14) The magnetic properties of the magnetic iron oxide particles, the composite particles and the black magnetic composite particles were measured using a vibration sample magnetometer "VSM-3S-15" (manufactured by Toei Kogyo Co., Ltd.) by applying an external magnetic field of 795.8 kA/m (10 kOe) thereto. Whereas, the magnetic Properties of the black magnetic toner were measured by applying external magnetic fields of 79.6 kA/m (1 kOe) and 795.8 kA/m (10 kOe) thereto.

Example 1

<Production of Black Magnetic Composite Particles>

20 kg of spherical magnetite particles (sphericity: 1.2; average particle size: 0.23 μm; geometrical standard deviation value: 1.42; BET specific surface area value: 9.2 m²/g; blackness (L* value): 20.6; fluidity index: 35; coercive force value: 4.9 kA/m (61 Oe); saturation magnetization value in a magnetic field of 795.8 kA/m (10 kOe): 84.9 Am²/kg (84.9 emu/g); residual magnetization value in a magnetic field of 795.8 kA/m (10 kOe): 7.8 Am²/kg (7.8 emu/g)), were deagglomerated in 150 liters of pure water using a stirrer, and further passed through a "TK pipeline homomixer" (tradename, manufactured by Tokushu Kika Kogyo Co., Ltd.) three times, thereby obtaining a slurry containing the spherical magnetite particles.

Successively, the obtained slurry containing the spherical magnetite particles was passed through a transverse-type sand grinder (tradename "MIGHTY MILL MHG-1.5L", manufactured by Inoue Seisakusho Co., Ltd.) five times at an axis-rotating speed of 2,000 rpm, thereby obtaining a slurry in which the spherical magnetite particles were dispersed.

The particles in the obtained slurry which remained on a sieve of 325 meshes (mesh size: 44 μm) was 0%. The slurry was filtered and washed with water, thereby obtaining a filter cake containing the spherical magnetite particles. After the obtained filter cake containing the spherical magnetite particles was dried at 120° C., 11.0 kg of the dried particles were then charged into an edge runner "MPUV-2 Model" (tradename, manufactured by Matsumoto Chuzo Tekkosho Co., Ltd.), and mixed and stirred at 294 N/cm (30 Kg/cm) and a stirring speed of 22 rpm for 30 minutes, thereby lightly deagglomerating the particles.

110 g of methyltriethoxysilane (tradename: "TSL8123", produced by GE Toshiba Silicone Co., Ltd.) was mixed and diluted with 200 ml of ethanol to obtain a methyltriethoxysilane solution. The methyltriethoxysilane solution was added to the deagglomerated spherical magnetite particles under the operation of the edge runner. The spherical magnetite particles were continuously mixed and stirred at a linear load of 392 N/CM (40 Kg/cm) and a stirring speed of 22 rpm for 60 minutes to form a coating layer composed of methyltriethoxysilane on the spherical magnetite particles.

Next, 1650 g of carbon black fine particles A (particle shape: granular shape; average particle size: 0.022μm; geometrical standard deviation value: 1.68; BET specific surface area value: 134 m²/g; DBP oil absorption: 89 ml/100 g; and blackness (L* value): 16.6) were added to the spherical magnetite particles coated with methyltriethoxysilane for 10 minutes while operating the edge runner. Further, the mixed particles were continuously stirred at a linear load of 392 N/cm (40 Kg/cm) and a stirring speed of 22 rpm for 60 minutes to form the carbon black coat on the coating layer composed of methyltriethoxysilane, thereby obtaining composite particles.

In order to determine the coating amount of methyltriethoxysilane and the amount of carbon black adhered, a part of the thus obtained composite particles was sampled, and heat-treated at 105° C. for 60 minutes using a drier. As a result, it was confirmed that the coating amount of methyltriethoxysilane was 0.15% by weight (calculated as Si), and the amount of carbon black adhered was 13.00% by weight (equivalent to 15 parts by weight based on 100 parts by weight of the spherical magnetite particles). Further, as a result of the observation of electron micrograph, it was confirmed that almost a whole amount of carbon black added was adhered onto the coating layer of an organosilane compound produced from the methyltriethoxysilane.

Next, 220 g of dimethylpolysiloxane (tradename: "TSF451", produced by GE Toshiba Silicone Co., Ltd.) was added to the above composite particles while operating an edge runner, and the obtained mixture was then mixed and stirred together at a linear load of 588 N/cm (60 Kg/cm) and a stirring speed of 22 rpm for 30 minutes, thereby obtaining composite particles on which dimethylpolysiloxane was uniformly adhered.

Next, 1,650 g of the above carbon black fine particles A were added to the above obtained particles for 10 minutes while operating the edge runner, and then mixed and stirred together at a linear load of 588 N/cm (60 Kg/cm) and a stirring speed of 22 rpm for 30 minutes, thereby bonding the second carbon black coat onto the first carbon black coat through the dimethylpolysiloxane as an adhesive. Thereafter, the obtained particles were heat-treated at 105° C. for 60 minutes using a drier, thereby obtaining black magnetic composite particles.

The obtained black magnetic composite particles had an average particle diameter of 0.24 μm, and a sphericity of 1.2:1 as shown in the electron photograph. In addition, the black magnetic composite particles showed a geometrical standard deviation of 1.42, a BET specific surface area value of 12.3 m²/g, fluidity index of 58, a blackness (L* value) of 17.6, and a desorption percentage of carbon black: 7.8%. The amount of the carbon black coat formed on the coating layer composed of the organosilane compound produced from methyl triethoxysilane is 26.01% by weight (calculated as C) based on the weight of the black magnetic composite particles (corresponding to 30 parts by weight based on 100 parts by weight of the spherical magnetite particles). The thickness of the carbon black coat formed was 0.0027 μm. The amount of dimethylpolysiloxanes adhered was 0.70% by weight (calculated as Si).

The obtained black magnetic composite particles had a coercive force value of 4.9 kA/m (61 Oe), a saturation magnetization value (in a magnetic field of 795.8 kA/m (10 kOe)) of 76.9 Am²/kg (76.9 emu/g), a residual magnetization value (in a magnetic field of 795.8 kA/m (10 kOe)) of 7.0 Am²/kg (7.0 emu/g), Since no carbon black were recognized-on the electron photograph, it was confirmed that a whole amount of the carbon black used contributed to the formation of the carbon black coat.

Example 2

<Production of Black Magnetic Toner Containing Black Magnetic Composite Particles>

450 g of the black magnetic composite particles obtained in Example 1, 550 g of styrene-butyl acrylate-methyl methacrylate copolymer resin (molecular weight=130,000, styrene/butyl acrylate/methyl methacrylate=82.0/16.5/1.5), 55 g of polypropylene wax (molecular weight: 3,000) and 15 g of a charge-controlling agent were charged into a Henschel mixer, and mixed and stirred therein at 60° C. for 15 minutes. The obtained mixed particles were melt-kneaded at 140° C. using a continuous-type twin-screw kneader (T-1), and the obtained kneaded material was cooled, coarsely pulverized and finely pulverized in air. The obtained particles were subjected to classification, thereby producing a black magnetic toner.

The obtained black magnetic toner had an average particle size of 9.9 μm, a dispersibility of 5th rank, a fluidity index of 84, a blackness (L* value) of 17.8, a volume resistivity of $8.4 \times 10^{13}$ Ω·cm, a coercive force value of 4.7 kA/m (59 Oe), a saturation magnetization value (in a magnetic field of 795.8 kA/m (10 kOe)) of 32.2 $Am^2/kg$ (32.2 emu/g), a residual magnetization value (in a magnetic field of 795.8 kA/m (10 kOe)) of 4.1 $Am^2/kg$ (4.1 emu/g), a saturation magnetization value (in a magnetic field of 79.6 kA/m (1 kOe)) of 25.3 $Am^2/kg$ (25.3 emu/g), and a residual magnetization value (in a magnetic field of 79.6 kA/m (1 kOe)) of 3.3 $Am^2/kg$ (3.3 emu/g).

Magnetic Iron Oxide Particles 1 to 4

Various magnetic iron oxide particles were prepared by known methods. The same procedure as defined in Example 1 was conducted by using the thus prepared particles, thereby obtaining deagglomerated magnetic iron oxide particles as core particles.

Various properties of the thus obtained magnetic iron oxide particles are shown in Table 1.

Magnetic Iron Oxide Particles 5

The same procedure as defined in Example 1 was conducted by using 20 kg of the deagglomerated octahedral magnetite particles (core particles 1) and 150 liters of water, thereby obtaining a slurry containing the octahedral magnetite particles. The pH value of the obtained re-dispersed slurry containing the octahedral magnetite particles was adjusted to 4.0 by adding acetic acid, and then the concentration of the slurry was adjusted to 98 g/liter by adding water thereto. After 150 liters of the slurry was heated to 60° C., 2722 ml of a 1.0 mol/liter aluminum sulfate solution (equivalent to 1.0% by weight (calculated as Al) based on the weight of the octahedral magnetite particles) was added to the slurry. After allowing the slurry to stand for 30 minutes, the pH value of the slurry was adjusted to 7.5 by adding an aqueous sodium hydroxide solution. Successively, 254 g of water glass #3 (equivalent to 0.5% by weight (calculated as $SiO_2$) based on the weight of the octahedral magnetite particles) was added to the slurry. After the slurry was aged for 30 minutes, the pH value of the slurry was adjusted to 7.5 by adding acetic acid. After further allowing the slurry to stand for 30 minutes, the slurry was subjected to filtration, washing with water, drying and pulverization, thereby obtaining the octahedral magnetite particles coated with hydroxides of aluminum and oxides of silicon.

Main production conditions are shown in Table 2, and various properties of the octahedral magnetite particles coated with hydroxides of aluminum and oxides of silicon are shown in Table 3.

Magnetic Iron Oxide Particles 6 to 8

The same procedure as defined in the production of the magnetic iron oxide particles 5 above, was conducted except that kind of magnetic iron oxide particles, and kind and amount of additives used in the surface treatment were varied, thereby obtaining surface-treated magnetic iron oxide particles.

Main production conditions are shown in Table 2, and various properties of the obtained surface-treated magnetic iron oxide particles are shown in Table 3.

Examples 3 to 14 and Comparative Examples 1 to 4

<Production of Composite Particles>

The same procedure as defined in Example 1 was conducted except that kind of magnetic iron oxide particles to be treated, addition or non-addition of an alkoxysilane compound or polysiloxane in the coating treatment with alkoxysilane compound or polysiloxane, kind and amount of the alkoxysilane compound or polysiloxane added, treating conditions of edge runner in the coating treatment, kind and amount of carbon black fine particles added in the first carbon black coat forming step, and treating conditions of edge runner used in the process for forming the first carbon black coat, were varied, thereby obtaining composite particles.

Various properties of the carbon black fine particles B to E are shown in Table 4.

Main production conditions are shown in Table 5, and various properties of the obtained composite particles are shown in Table 6.

The composite particles obtained in Examples 3 to 14 were observed by an electron microscope. As a result, almost no independent carbon black was recognized. Therefore, it was confirmed that a substantially whole amount of the carbon black contributed to the formation of the first carbon black coat on the coating layer composed of organosilane compound produced from the alkoxysilane compound or polysiloxane.

Meanwhile, all the additives used in Examples 11 to 13 were polysiloxanes. Specifically, "TSF484" (tradename, produced by GE Toshiba Silicone Co., Ltd.) was methyl hydrogen polysiloxane; "BYK-080" (tradename, produced by BYK-Chemie Japan Co., Ltd.) was modified polysiloxane; and "TSF-4770" (tradename, produced by GE Toshiba Silicone Co., Ltd.) was carboxylic acid-terminal-modified polysiloxane.

Examples 15 to 26 and Comparative Examples 5 to 11

<Production of Black Magnetic Composite Particles>

The same procedure as defined in Example 1 was conducted except that kind of composite particles, kind and amount of adhesive added, edge runner treatment conditions used in the adhesive-treating step, kind and amount of carbon black fine particles added in the second carbon black coat-adhering step, and edge runner treatment conditions used in the second carbon black coat-adhering step, were changed variously, thereby obtaining black magnetic composite particles.

Meanwhile, as a result of observing the black magnetic composite particles obtained in Examples 15 to 26 by an electron microscope, no liberated carbon black was recognized. Therefore, it was confirmed that almost a whole amount of carbon black added was adhered onto the first carbon black coat.

Main treatment conditions are shown in Table 7, and various properties of the obtained black magnetic composite particles are shown in Table 8.

Examples 27 to 38 and Comparative Examples 12 to 23

<Production of Black Magnetic Toner>

The same procedure as defined in Example 2 was conducted by using the black magnetic composite particles obtained in Examples 15 to 26, composite particles obtained in Example 5, Core particles 1 to 4, and Comparative Examples 3 and 5 to 11, thereby obtaining black magnetic toners.

Main production conditions are shown in Table 9 and various properties of the obtained black magnetic toners are shown in Tables 10 to 11.

TABLE 1

| Magnetic iron oxide particles | Properties of magnetic iron oxide particles | |
|---|---|---|
| | Kind | Particle shape |
| Magnetic iron oxide particles 1 | Magnetite particles | Octahedral |
| Magnetic iron oxide particles 2 | Magnetite particles | Spherical |
| Magnetic iron oxide particles 3 | Magnetite particles | Acicular |
| Magnetic iron oxide particles 4 | Maghemite particles | Spherical |

| Magnetic iron oxide particles | Properties of magnetic iron oxide particles | | |
|---|---|---|---|
| | Average particle size (major axial diameter) ($\mu$m) | Sphericity (aspect ratio) (−) | Geometrical standard deviation value (−) |
| Magnetic iron oxide particles 1 | 0.28 | — | 1.53 |
| Magnetic iron oxide particles 2 | 0.23 | 1.2:1 | 1.35 |
| Magnetic iron oxide particles 3 | 0.40 | 7.8:1 | 1.53 |
| Magnetic iron oxide particles 4 | 0.20 | 1.2:1 | 1.42 |

| Magnetic iron oxide particles | Properties of magnetic iron oxide particles | | |
|---|---|---|---|
| | BET specific surface area ($m^2$/g) | Magnetic properties Coercive force value (kA/m) | (Oe) |
| Magnetic iron oxide particles 1 | 4.6 | 8.0 | 101 |
| Magnetic iron oxide particles 2 | 11.8 | 5.0 | 63 |
| Magnetic iron oxide particles 3 | 18.8 | 27.3 | 343 |
| Magnetic iron oxide particles 4 | 7.2 | 4.3 | 54 |

| Magnetic iron oxide particles | Properties of magnetic iron oxide particles Magnetic properties | | | |
|---|---|---|---|---|
| | Saturation magnetization value (795.8 kA/m) (10 kOe) | | Residual magnetization value (795.8 kA/m) (10 kOe) | |
| | ($Am^2$/kg) | (emu/g) | ($Am^2$/kg) | (emu/g) |
| Magnetic iron oxide particles 1 | 86.8 | 86.8 | 12.2 | 12.2 |
| Magnetic iron oxide particles 2 | 85.1 | 85.1 | 7.7 | 7.7 |
| Magnetic iron oxide particles 3 | 86.3 | 86.3 | 29.3 | 29.3 |
| Magnetic iron oxide particles 4 | 78.8 | 78.8 | 8.7 | 8.7 |

TABLE 1-continued

| Magnetic iron oxide particles | Properties of magnetic iron oxide particles | |
|---|---|---|
| | Fluidity index (−) | Blackness (L* value) (−) |
| Magnetic iron oxide particles 1 | 34 | 20.3 |
| Magnetic iron oxide particles 2 | 38 | 20.1 |
| Magnetic iron oxide particles 3 | 32 | 23.8 |
| Magnetic iron oxide particles 4 | 38 | 31.5 |

TABLE 2

| Magnetic iron oxide particles | Kind of magnetic iron oxide particles | Surface-treatment step Additives | | |
|---|---|---|---|---|
| | | Kind | Calculated as | Amount (wt. %) |
| Magnetic iron oxide particles 5 | Magnetic iron oxide particles 1 | Aluminum sulfate | Al | 1.0 |
| | | Water glass #3 | $SiO_2$ | 0.5 |
| Magnetic iron oxide particles 6 | Magnetic iron oxide particles 2 | Sodium aluminate | Al | 2.0 |
| | | Colloidal silica | $SiO_2$ | 1.0 |
| Magnetic iron oxide particles 7 | Magnetic iron oxide particles 3 | Aluminum acetate | Al | 5.0 |
| Magnetic iron oxide particles 8 | Magnetic iron oxide particles 4 | Water glass #3 | $SiO_2$ | 1.0 |

| Magnetic iron oxide particles | Surface-treatment step Coating material | | |
|---|---|---|---|
| | Kind | Calculated as | Amount (wt. %) |
| Magnetic iron oxide particles 5 | A | Al | 0.98 |
| | S | $SiO_2$ | 0.49 |
| Magnetic iron oxide particles 6 | A | Al | 1.92 |
| | S | $SiO_2$ | 0.96 |
| Magnetic iron oxide particles 7 | A | Al | 4.75 |
| Magnetic iron oxide particles 8 | S | SiO2 | 0.98 |

Note;
A: Hydroxide of aluminum
S: Oxide of silicon

TABLE 3

Properties of surface-treated magnetic iron oxide particles

| Magnetic iron oxide particles | Average particle size (major axial diameter) ($\mu$m) | Sphericity (aspect ratio) (-) | Geometrical standard deviation value (-) |
|---|---|---|---|
| Magnetic iron oxide particles 5 | 0.29 | — | 1.51 |
| Magnetic iron oxide particles 6 | 0.24 | 1.2:1 | 1.35 |
| Magnetic iron oxide particles 7 | 0.40 | 7.8:1 | 1.52 |
| Magnetic iron oxide particles 8 | 0.20 | 1.2:1 | 1.42 |

Properties of surface-treated magnetic iron oxide particles

| Magnetic iron oxide particles | BET specific surface area ($m^2$/g) | Magnetic properties Coercive force value (kA/m) | (Oe) |
|---|---|---|---|
| Magnetic iron oxide particles 5 | 9.8 | 8.2 | 103 |
| Magnetic iron oxide particles 6 | 13.6 | 4.9 | 61 |
| Magnetic iron oxide particles 7 | 25.4 | 26.7 | 336 |
| Magnetic iron oxide particles 8 | 7.5 | 4.2 | 53 |

Properties of surface-treated magnetic iron oxide particles — Magnetic properties

| Magnetic iron oxide particles | Saturation magnetization value (795.8 kA/m) (10 kOe) ($Am^2$/kg) | (emu/g) | Residual magnetization value (795.8 kA/m) (10 kOe) ($Am^2$/kg) | (emu/g) |
|---|---|---|---|---|
| Magnetic iron oxide particles 5 | 86.3 | 86.3 | 12.1 | 12.1 |
| Magnetic iron oxide particles 6 | 84.8 | 84.8 | 7.6 | 7.6 |
| Magnetic iron oxide particles 7 | 86.0 | 86.0 | 29.1 | 29.1 |
| Magnetic iron oxide particles 8 | 78.6 | 78.6 | 8.6 | 8.6 |

Properties of surface-treated magnetic iron oxide particles

| Magnetic iron oxide particles | Fluidity index (-) | Blackness (L* value) (-) |
|---|---|---|
| Magnetic iron oxide particles 5 | 32 | 21.4 |
| Magnetic iron oxide particles 6 | 37 | 20.8 |
| Magnetic iron oxide particles 7 | 32 | 24.6 |
| Magnetic iron oxide particles 8 | 37 | 31.6 |

TABLE 4

| Kind of carbon black fine particles | Properties of carbon black fine particles Particle shape | Average particle size ($\mu$m) |
|---|---|---|
| Carbon black B | Granular | 0.022 |
| Carbon black C | Granular | 0.015 |
| Carbon black D | Granular | 0.030 |
| Carbon black E | Granular | 0.028 |

| Kind of carbon black fine particles | Properties of carbon black fine particles Geometrical standard deviation value (-) | BET specific surface area ($m^2$/g) |
|---|---|---|
| Carbon black B | 1.78 | 133.5 |
| carbon black C | 1.56 | 265.3 |
| Carbon black D | 2.06 | 84.6 |
| Carbon black E | 1.71 | 800.0 |

| Kind of carbon black fine particles | Properties of carbon black fine particles DBP oil absorption (ml/100 g) | Blackness (L* value) (-) |
|---|---|---|
| Carbon black B | 84 | 14.6 |
| Carbon black C | 57 | 15.2 |
| Carbon black D | 95 | 17.0 |
| Carbon black E | 200 | 15.3 |

TABLE 5

| Examples and Comparative Examples | Kind of magnetic iron oxide particles | Production of composite particles Coating with alkoxysilane or polysiloxane Additives Kind | Amount added (part by weight) |
|---|---|---|---|
| Example 3 | Magnetic iron oxide particles 1 | Methyl triethoxysilane | 2.0 |
| Example 4 | Magnetic iron oxide particles 2 | Methyl trimethoxysilane | 1.5 |
| Example 5 | Magnetic iron oxide particles 3 | Dimethyl dimethoxysilane | 0.5 |
| Example 6 | Magnetic iron oxide particles 4 | Phenyl triethoxysilane | 1.5 |
| Example 7 | Magnetic iron | Isobutyl | 2.0 |

TABLE 5-continued

| Examples | | | |
|---|---|---|---|
| Example 8 | Magnetic iron oxide particles 5 | Methyl trimethoxysilane | 3.0 |
| Example 9 | Magnetic iron oxide particles 6 | Methyl triethoxysilane | 5.0 |
| Example 10 | Magnetic iron oxide particles 7 | Methyl trimethoxysilane | 1.0 |
| Example 11 | Magnetic iron oxide particles 8 | Methyl trimethoxysilane | 1.0 |
| Example 12 | Magnetic iron oxide particles 1 | TSF484 | 1.0 |
| Example 13 | Magnetic iron oxide particles 1 | BYK-080 | 1.0 |
| Example 14 | Magnetic iron oxide particles 1 | TSF4770 | 2.0 |
| Comparative Example 1 | Magnetic iron oxide particles 1 | Methyl triethoxysilane | 1.0 |
| Comparative Example 2 | Magnetic iron oxide particles 1 | — | — |
| Comparative Example 3 | Magnetic iron oxide particles 1 | Methyl triethoxysilane | 0.005 |
| Comparative Example 4 | Magnetic iron oxide particles 1 | Methyl triethoxysilane | 1.0 |
|  | Magnetic iron oxide particles 1 | γ-aminopropyl triethoxysilane | 1.0 |

| Examples and Comparative Examples | Production of composite particles Coating with alkoxysilane or polysiloxane | | |
|---|---|---|---|
| | Edge runner treatment | | Coating amount |
| | Linear load | Time | (calculated as Si) |
| | (N/cm) | (Kg/cm) | (min.) | (wt. %) |
| Example 3 | 392 | 40 | 30 | 0.30 |
| Example 4 | 588 | 60 | 20 | 0.30 |
| Example 5 | 392 | 40 | 30 | 0.11 |
| Example 6 | 784 | 80 | 30 | 0.17 |
| Example 7 | 294 | 30 | 20 | 0.30 |
| Example 8 | 588 | 60 | 30 | 0.45 |
| Example 9 | 441 | 45 | 20 | 0.96 |
| Example 10 | 294 | 30 | 60 | 0.20 |
| Example 11 | 588 | 60 | 30 | 0.42 |
| Example 12 | 588 | 60 | 60 | 0.17 |
| Example 13 | 588 | 60 | 30 | 0.69 |
| Example 14 | 588 | 60 | 30 | 0.15 |
| Comparative Example 1 | — | — | — | — |
| Comparative Example 2 | 588 | 60 | 30 | $7 \times 10^{-4}$ |
| Comparative Example 3 | 588 | 60 | 30 | 0.15 |
| Comparative Example 4 | 588 | 60 | 60 | 0.12 |

| Examples and Comparative Examples | Production of composite particles Adhesion step with first carbon black coat Carbon black | |
|---|---|---|
| | Kind | Amount adhered (part by weight) |
| Example 3 | B | 15.0 |
| Example 4 | C | 20.0 |
| Example 5 | D | 25.0 |
| Example 6 | B | 20.0 |
| Example 7 | C | 15.0 |
| Example 8 | D | 18.0 |
| Example 9 | B | 15.0 |
| Example 10 | C | 15.0 |
| Example 11 | B | 15.0 |
| Example 12 | B | 10.0 |
| Example 13 | B | 15.0 |
| Example 14 | E | 15.0 |
| Comparative Example 1 | B | 15.0 |
| Comparative Example 2 | B | 15.0 |
| Comparative Example 3 | C | 30.0 |
| Comparative Example 4 | D | 15.0 |

| Examples and Comparative Examples | Production of composite particles Adhesion step with first carbon black coat | | | |
|---|---|---|---|---|
| | Edge runner treatment | | | Amount adhered |
| | Linear load | | Time | (calculated as C) |
| | (N/cm) | (Kg/cm) | (min.) | (wt. %) |
| Example 3 | 588 | 60 | 30 | 13.00 |
| Example 4 | 294 | 30 | 30 | 16.59 |
| Example 5 | 392 | 40 | 30 | 19.94 |
| Example 6 | 588 | 60 | 20 | 16.61 |
| Example 7 | 588 | 60 | 20 | 13.03 |
| Example 8 | 294 | 30 | 30 | 15.22 |
| Example 9 | 441 | 45 | 45 | 13.01 |
| Example 10 | 686 | 70 | 30 | 12.98 |
| Example 11 | 294 | 30 | 60 | 13.01 |
| Example 12 | 588 | 60 | 20 | 9.05 |
| Example 13 | 588 | 60 | 30 | 13.02 |
| Example 14 | 588 | 60 | 30 | 13.00 |
| Comparative Example 1 | 588 | 60 | 30 | 13.00 |
| Comparative Example 2 | 588 | 60 | 30 | 13.01 |
| Comparative Example 3 | 588 | 60 | 30 | 23.02 |
| Comparative Example 4 | 588 | 60 | 30 | 13.01 |

TABLE 6

| Examples and Comparative Examples | Properties of composite particles | | |
|---|---|---|---|
| | Average particle size ($\mu$m) | Aspect ratio (sphericity) (–) | Geometrical standard deviation value (–) |
| Example 3 | 0.29 | — | 1.53 |
| Example 4 | 0.25 | 1.2:1 | 1.35 |
| Example 5 | 0.42 | 7.8:1 | 1.53 |
| Example 6 | 0.22 | 1.2:1 | 1.42 |
| Example 7 | 0.30 | — | 1.53 |
| Example 8 | 0.26 | 1.2:1 | 1.35 |
| Example 9 | 0.41 | 7.7:1 | 1.53 |
| Example 10 | 0.21 | 1.2:1 | 1.42 |
| Example 11 | 0.29 | — | 1.53 |
| Example 12 | 0.29 | — | 1.52 |
| Example 13 | 0.29 | — | 1.53 |
| Example 14 | 0.29 | — | 1.53 |
| Comparative Example 1 | 0.28 | — | — |
| Comparative Example 2 | 0.28 | — | — |
| Comparative Example 3 | 0.30 | — | — |
| Comparative Example 4 | 0.29 | — | — |

| Examples and Comparative Examples | Properties of composite particles | | |
|---|---|---|---|
| | BET specific surface area ($m^2$/g) | Magnetic properties Coercive force value | |
| | | (kA/m) | (Oe) |
| Example 3 | 6.8 | 8.0 | 100 |
| Example 4 | 12.1 | 4.9 | 61 |
| Example 5 | 19.1 | 26.9 | 338 |
| Example 6 | 9.6 | 4.2 | 53 |
| Example 7 | 10.1 | 8.0 | 101 |
| Example 8 | 14.1 | 4.8 | 60 |

TABLE 6-continued

| | | | |
|---|---|---|---|
| Example 9 | 25.3 | 26.4 | 332 |
| Example 10 | 7.9 | 4.0 | 50 |
| Example 11 | 4.8 | 7.9 | 99 |
| Example 12 | 5.3 | 8.3 | 104 |
| Example 13 | 6.8 | 8.2 | 103 |
| Example 14 | 7.2 | 8.1 | 102 |
| Comparative Example 1 | 18.3 | 8.0 | 101 |
| Comparative Example 2 | 16.5 | 8.2 | 103 |
| Comparative Example 3 | 13.8 | 8.0 | 100 |
| Comparative Example 4 | 18.6 | 8.3 | 104 |

Properties of composite particles
Magnetic properties

| Examples and Comparative Examples | Saturation magnetization value (795.8 kA/m) (10 kOe) | | Residual magnetization value (795.8 kA/m) (10 kOe) | |
|---|---|---|---|---|
| | $(Am^2/kg)$ | (emu/g) | $(Am^2/kg)$ | (emu/g) |
| Example 3 | 73.6 | 73.6 | 9.9 | 9.9 |
| Example 4 | 72.9 | 72.9 | 6.3 | 6.3 |
| Example 5 | 69.3 | 69.3 | 14.1 | 14.1 |
| Example 6 | 70.2 | 70.2 | 7.1 | 7.1 |
| Example 7 | 71.4 | 71.4 | 10.8 | 10.8 |
| Example 8 | 73.2 | 73.2 | 7.0 | 7.0 |
| Example 9 | 72.6 | 72.6 | 15.6 | 15.6 |
| Example 10 | 73.8 | 73.8 | 7.3 | 7.3 |
| Example 11 | 73.3 | 73.3 | 10.3 | 10.3 |
| Example 12 | 74.1 | 74.1 | 10.2 | 10.2 |
| Example 13 | 73.5 | 73.5 | 10.1 | 10.1 |
| Example 14 | 73.8 | 73.8 | 10.2 | 10.2 |
| Comparative Example 1 | 73.4 | 73.4 | 10.0 | 10.0 |
| Comparative Example 2 | 73.6 | 73.6 | 10.3 | 10.3 |
| Comparative Example 3 | 73.6 | 73.6 | 10.3 | 10.3 |
| Comparative Example 4 | 73.8 | 73.8 | 10.2 | 10.2 |

| Examples and Comparative Examples | Properties of composite particles | | |
|---|---|---|---|
| | Fluidity index (−) | Blackness (L* value) (−) | Carbon black desorption percentage (%) |
| Example 3 | 50 | 17.0 | 8.6 |
| Example 4 | 47 | 16.3 | 7.2 |
| Example 5 | 46 | 17.8 | 8.3 |
| Example 6 | 52 | 17.9 | 9.6 |
| Example 7 | 51 | 16.3 | 4.8 |
| Example 8 | 49 | 17.4 | 4.6 |
| Example 9 | 48 | 17.3 | 3.3 |
| Example 10 | 50 | 18.1 | 2.1 |
| Example 11 | 52 | 17.1 | 7.3 |
| Example 12 | 50 | 17.5 | 6.4 |
| Example 13 | 52 | 16.9 | 6.1 |
| Example 14 | 47 | 17.2 | 9.8 |
| Comparative Example 1 | 38 | 19.6 | 59.8 |
| Comparative Example 2 | 41 | 19.5 | 40.2 |
| Comparative Example 3 | 38 | 16.5 | 36.4 |
| Comparative Example 4 | 37 | 19.6 | 41.3 |

TABLE 7

| Examples and Comparative Examples | Kind of composite particles | Production of black magnetic composite particles Treatment step with adhesive Additives | |
|---|---|---|---|
| | | Kind | Amount added (part by weight) |
| Example 15 | Example 3 | Dimethylpolysiloxane | 1.0 |
| Example 16 | Example 4 | Dimethylpolysiloxane | 2.0 |
| Example 17 | Example 5 | Dimethylpolysiloxane | 1.0 |
| Example 18 | Example 6 | Dimethylpolysiloxane | 2.0 |
| Example 19 | Example 7 | Dimethylpolysiloxane | 1.0 |
| Example 20 | Example 8 | Dimethylpolysiloxane | 2.0 |
| Example 21 | Example 9 | Dimethylpolysiloxane | 1.0 |
| Example 22 | Example 10 | Dimethylpolysiloxane | 2.0 |
| Example 23 | Example 11 | Dimethylpolysiloxane | 1.0 |
| Example 24 | Example 12 | Dimethylpolysiloxane | 1.5 |
| Example 25 | Example 13 | Dimethylpolysiloxane | 2.0 |
| Example 26 | Example 14 | Dimethylpolysiloxane | 1.0 |
| Comparative Example 5 | Comparative Example 1 | Dimethylpolysiloxane | 1.0 |
| Comparative Example 6 | Comparative Example 2 | Dimethylpolysiloxane | 1.0 |
| Comparative Example 7 | Comparative Example 3 | Dimethylpolysiloxane | 1.0 |
| Comparative Example 8 | Comparative Example 4 | Dimethylpolysiloxane | 1.0 |
| Comparative Example 9 | Example 3 | — | — |
| Comparative Example 10 | Example 3 | Dimethylpolysiloxane | 0.01 |
| Comparative Example 11 | Example 3 | Methyl triethoxysilane | 1.0 |

| Examples and Comparative Examples | Production of black magnetic composite particles Treatment step with adhesive | | |
|---|---|---|---|
| | Edge runner treatment | | Coating amount |
| | Linear load | Time | (calculated as Si) |
| | (N/cm) | (Kg/cm) (min.) | (wt. %) |
| Example 15 | 392 | 40 30 | 0.33 |
| Example 16 | 588 | 60 20 | 0.70 |
| Example 17 | 441 | 45 30 | 0.32 |
| Example 18 | 735 | 75 20 | 0.71 |
| Example 19 | 294 | 30 30 | 0.32 |
| Example 20 | 588 | 60 60 | 0.68 |
| Example 21 | 735 | 75 30 | 0.32 |
| Example 22 | 588 | 60 20 | 0.70 |
| Example 23 | 294 | 30 60 | 0.34 |
| Example 24 | 392 | 40 30 | 0.51 |
| Example 25 | 490 | 50 20 | 0.69 |
| Example 26 | 588 | 60 30 | 0.33 |
| Comparative Example 5 | 588 | 60 30 | 0.33 |
| Comparative Example 6 | 588 | 60 30 | 0.32 |
| Comparative Example 7 | 588 | 60 30 | 0.33 |
| Comparative Example 8 | 588 | 60 30 | 0.32 |
| Comparative Example 9 | — | — — | — |
| Comparative Example 10 | 588 | 60 30 | $3 \times 10^{-3}$ |
| Comparative Example 11 | 588 | 60 30 | 0.15 |

| Examples and Comparative Examples | Production of black magnetic composite particles Adhesion step with second carbon black coat Carbon black | |
|---|---|---|
| | Kind | Amount adhered (part by weight) |
| Example 15 | B | 15.0 |
| Example 16 | C | 18.0 |

TABLE 7-continued

| | | |
|---|---|---|
| Example 17 | B | 20.0 |
| Example 18 | C | 15.0 |
| Example 19 | B | 18.0 |
| Example 20 | C | 20.0 |
| Example 21 | B | 20.0 |
| Example 22 | C | 20.0 |
| Example 23 | B | 20.0 |
| Example 24 | B | 20.0 |
| Example 25 | B | 15.0 |
| Example 26 | E | 15.0 |
| Comparative Example 5 | B | 15.0 |
| Comparative Example 6 | B | 15.0 |
| Comparative Example 7 | C | 15.0 |
| Comparative Example 8 | C | 15.0 |
| Comparative Example 9 | B | 15.0 |
| Comparative Example 10 | C | 15.0 |
| Comparative Example 11 | B | 15.0 |

| | Production of black magnetic composite particles Adhesion step with second carbon black coat | | |
|---|---|---|---|
| Examples and Comparative Examples | Edge runner treatment | | Amount adhered (calculated as C) (wt. %) |
| | Linear load | Time | |
| | (N/cm) | (Kg/cm) | (min.) |
| Example 15 | 588 | 60 | 30 | 13.01 |
| Example 16 | 294 | 30 | 30 | 15.20 |
| Example 17 | 392 | 40 | 20 | 16.62 |
| Example 18 | 196 | 20 | 30 | 13.01 |
| Example 19 | 588 | 60 | 30 | 15.19 |
| Example 20 | 392 | 40 | 40 | 16.61 |
| Example 21 | 784 | 80 | 20 | 16.64 |
| Example 22 | 196 | 20 | 30 | 16.63 |
| Example 23 | 735 | 75 | 30 | 16.63 |
| Example 24 | 441 | 45 | 60 | 16.61 |
| Example 25 | 588 | 60 | 30 | 13.00 |
| Example 26 | 588 | 60 | 30 | 13.01 |
| Comparative Example 5 | 588 | 60 | 30 | 13.01 |
| Comparative Example 6 | 588 | 60 | 30 | 12.99 |
| Comparative Example 7 | 588 | 60 | 30 | 13.02 |
| Comparative Example 8 | 588 | 60 | 30 | 13.01 |
| Comparative Example 9 | 588 | 60 | 30 | 13.00 |
| Comparative Example 10 | 588 | 60 | 30 | 13.00 |
| Comparative Example 11 | 588 | 60 | 30 | 13.01 |

TABLE 8

| | Properties of black magnetic composite particles | | |
|---|---|---|---|
| Examples and Comparative Examples | Average particle size ($\mu$m) | Aspect ratio (sphericity) (-) | Geometrical standard deviation value (-) |
| Example 15 | 0.30 | — | 1.53 |
| Example 16 | 0.26 | 1.2:1 | 1.35 |
| Example 17 | 0.43 | 7.8:1 | 1.53 |
| Example 18 | 0.23 | 1.2:1 | 1.42 |
| Example 19 | 0.31 | — | 1.53 |
| Example 20 | 0.28 | 1.2:1 | 1.36 |
| Example 21 | 0.43 | 7.7:1 | 1.53 |
| Example 22 | 0.23 | 1.2:1 | 1.43 |
| Example 23 | 0.30 | — | 1.53 |
| Example 24 | 0.30 | — | 1.53 |
| Example 25 | 0.30 | — | 1.53 |
| Example 26 | 0.30 | — | 1.53 |
| Comparative Example 5 | 0.29 | — | — |
| Comparative Example 6 | 0.29 | — | — |
| Comparative Example 7 | 0.31 | — | — |
| Comparative Example 8 | 0.30 | — | — |
| Comparative Example 9 | 0.29 | — | — |
| Comparative Example 10 | 0.29 | — | — |
| Comparative Example 11 | 0.30 | — | — |

| | Properties of black magnetic composite particles | | |
|---|---|---|---|
| Examples and Comparative Examples | BET specific surface area ($m^2$/g) | Magnetic properties Coercive force value | |
| | | (kA/m) | (Oe) |
| Example 15 | 7.3 | 7.9 | 99 |
| Example 16 | 13.2 | 4.8 | 60 |
| Example 17 | 19.6 | 26.5 | 333 |
| Example 18 | 9.8 | 4.1 | 51 |
| Example 19 | 10.9 | 8.0 | 100 |
| Example 20 | 14.6 | 4.8 | 60 |
| Example 21 | 26.1 | 26.1 | 328 |
| Example 22 | 8.9 | 4.1 | 51 |
| Example 23 | 5.8 | 8.0 | 101 |
| Example 24 | 6.3 | 8.0 | 100 |
| Example 25 | 7.1 | 8.2 | 103 |
| Example 26 | 7.8 | 8.0 | 101 |
| Comparative Example 5 | 21.6 | 8.3 | 104 |
| Comparative Example 6 | 19.3 | 8.4 | 105 |
| Comparative Example 7 | 17.6 | 8.4 | 106 |
| Comparative Example 8 | 23.8 | 8.1 | 102 |
| Comparative Example 9 | 11.4 | 8.0 | 101 |
| Comparative Example 10 | 10.5 | 8.0 | 101 |
| Comparative Example 11 | 10.0 | 8.0 | 101 |

| | Properties of black magnetic composite particles Magnetic properties | | | |
|---|---|---|---|---|
| Examples and Comparative Examples | Saturation magnetization value (795.8 kA/m) (10 kOe) | | Residual magnetization value (795.8 kA/m) (10 kOe) | |
| | (Am$^2$/kg) | (emu/g) | (Am$^2$/kg) | (emu/g) |
| Example 15 | 63.2 | 63.2 | 8.3 | 8.3 |
| Example 16 | 64.6 | 64.6 | 5.9 | 5.9 |
| Example 17 | 60.1 | 60.1 | 12.1 | 12.1 |
| Example 18 | 60.9 | 60.9 | 6.0 | 6.0 |
| Example 19 | 63.2 | 63.2 | 8.1 | 8.1 |
| Example 20 | 62.1 | 62.1 | 6.3 | 6.3 |
| Example 21 | 63.8 | 63.8 | 12.9 | 12.9 |
| Example 22 | 64.1 | 64.1 | 6.5 | 6.5 |
| Example 23 | 62.8 | 62.8 | 8.3 | 8.3 |
| Example 24 | 63.4 | 63.4 | 8.2 | 8.2 |
| Example 25 | 63.6 | 63.6 | 8.1 | 8.1 |
| Example 26 | 63.5 | 63.5 | 8.2 | 8.2 |
| Comparative Example 5 | 64.3 | 64.3 | 8.0 | 8.0 |

TABLE 8-continued

| | | | | |
|---|---|---|---|---|
| Comparative Example 6 | 63.2 | 63.2 | 8.3 | 8.3 |
| Comparative Example 7 | 61.3 | 61.3 | 8.3 | 8.3 |
| Comparative Example 8 | 60.9 | 60.9 | 8.1 | 8.1 |
| Comparative Example 9 | 63.2 | 63.2 | 8.3 | 8.3 |
| Comparative Example 10 | 63.3 | 63.3 | 8.2 | 8.2 |
| Comparative Example 11 | 63.3 | 63.3 | 8.3 | 8.3 |

| Examples and Comparative Examples | Properties of black magnetic composite particles | | |
|---|---|---|---|
| | Fluidity index (−) | Blackness (L* value) (−) | Carbon black desorption percentage (%) |
| Example 15 | 58 | 16.7 | 6.8 |
| Example 16 | 56 | 16.1 | 7.1 |
| Example 17 | 55 | 16.5 | 6.8 |
| Example 18 | 60 | 17.7 | 7.9 |
| Example 19 | 60 | 16.0 | 3.2 |
| Example 20 | 58 | 17.1 | 2.6 |
| Example 21 | 57 | 16.9 | 4.0 |
| Example 22 | 59 | 17.8 | 1.8 |
| Example 23 | 61 | 16.7 | 5.9 |
| Example 24 | 59 | 17.1 | 7.3 |
| Example 25 | 60 | 16.6 | 8.6 |
| Example 26 | 55 | 17.0 | 10.8 |
| Comparative Example 5 | 41 | 18.8 | 63.2 |
| Comparative Example 6 | 43 | 18.9 | 52.2 |
| Comparative Example 7 | 41 | 18.6 | 39.8 |
| Comparative Example 8 | 40 | 19.0 | 34.4 |
| Comparative Example 9 | 39 | 16.9 | 53.8 |
| Comparative Example 10 | 40 | 16.9 | 47.6 |
| Comparative Example 11 | 43 | 16.8 | 21.2 |

| Examples and Comparative Examples | Properties of black magnetic composite particles Carbon black coat | |
|---|---|---|
| | Amount (part by weight) | Thickness (μm) |
| Example 15 | 30.0 | 0.0027 |
| Example 16 | 38.0 | 0.0029 |
| Example 17 | 45.0 | 0.0030 |
| Example 18 | 35.0 | 0.0028 |
| Example 19 | 33.0 | 0.0027 |
| Example 20 | 38.0 | 0.0028 |
| Example 21 | 35.0 | 0.0028 |
| Example 22 | 35.0 | 0.0028 |
| Example 23 | 35.0 | 0.0028 |
| Example 24 | 30.0 | 0.0027 |
| Example 25 | 30.0 | 0.0027 |
| Example 26 | 30.0 | 0.0027 |
| Comparative Example 5 | 30.0 | — |
| Comparative Example 6 | 30.0 | — |
| Comparative Example 7 | 45.0 | — |
| Comparative Example 8 | 30.0 | — |
| Comparative Example 9 | 30.0 | — |
| Comparative Example 10 | 30.0 | — |
| Comparative Example 11 | 30.0 | — |

TABLE 9

| Examples and Comparative Examples | Production of black magnetic toner Magnetic particles | |
|---|---|---|
| | Kind | Amount blended (part by weight) |
| Example 27 | Example 15 | 45 |
| Example 28 | Example 16 | 45 |
| Example 29 | Example 17 | 45 |
| Example 30 | Example 18 | 45 |
| Example 31 | Example 19 | 45 |
| Example 32 | Example 20 | 45 |
| Example 33 | Example 21 | 45 |
| Example 34 | Example 22 | 45 |
| Example 35 | Example 23 | 45 |
| Example 36 | Example 24 | 45 |
| Example 37 | Example 25 | 45 |
| Example 38 | Example 26 | 45 |
| Comparative Example 12 | Core particles 1 | 45 |
| Comparative Example 13 | Core particles 2 | 45 |
| Comparative Example 14 | Core particles 3 | 45 |
| Comparative Example 15 | Core particles 4 | 45 |
| Comparative Example 16 | Comparative Example 3 | 45 |
| Comparative Example 17 | Comparative Example 5 | 45 |
| Comparative Example 18 | Comparative Example 6 | 45 |
| Comparative Example 19 | Comparative Example 7 | 45 |
| Comparative Example 20 | Comparative Example 8 | 45 |
| Comparative Example 21 | Comparative Example 9 | 45 |
| Comparative Example 22 | Comparative Example 10 | 45 |
| Comparative Example 23 | Comparative Example 11 | 45 |

| Examples and Comparative Examples | Production of black magnetic toner Resin | |
|---|---|---|
| | Kind | Amount blended (part by weight) |
| Example 27 | Styrene-acrylic copolymer | 55 |
| Example 28 | Styrene-acrylic copolymer | 55 |
| Example 29 | Styrene-acrylic copolymer | 55 |
| Example 30 | Styrene-acrylic copolymer | 55 |
| Example 31 | Styrene-acrylic copolymer | 55 |
| Example 32 | Styrene-acrylic copolymer | 55 |
| Example 33 | Styrene-acrylic copolymer | 55 |
| Example 34 | Styrene-acrylic copolymer | 55 |
| Example 35 | Styrene-acrylic copolymer | 55 |
| Example 36 | Styrene-acrylic copolymer | 55 |
| Example 37 | Styrene-acrylic copolymer | 55 |
| Example 38 | Styrene-acrylic copolymer | 55 |
| Comparative Example 12 | Styrene-acrylic copolymer | 55 |
| Comparative Example 13 | Styrene-acrylic copolymer | 55 |
| Comparative Example 14 | Styrene-acrylic copolymer | 55 |
| Comparative Example 15 | Styrene-acrylic copolymer | 55 |
| Comparative Example 16 | Styrene-acrylic copolymer | 55 |
| Comparative Example 17 | Styrene-acrylic copolymer | 55 |
| Comparative Example 18 | Styrene-acrylic copolymer | 55 |
| Comparative Example 19 | Styrene-acrylic copolymer | 55 |
| Comparative Example 20 | Styrene-acrylic copolymer | 55 |
| Comparative Example 21 | Styrene-acrylic copolymer | 55 |
| Comparative Example 22 | Styrene-acrylic copolymer | 55 |
| Comparative Example 23 | Styrene-acrylic copolymer | 55 |

TABLE 10

| Examples | Properties of black magnetic toner | | |
|---|---|---|---|
| | Average particle size (μm) | Dispersibility (−) | Fluidity index (−) |
| Example 27 | 9.8 | 5 | 84 |
| Example 28 | 10.0 | 5 | 84 |
| Example 29 | 10.1 | 5 | 83 |
| Example 30 | 9.9 | 5 | 86 |
| Example 31 | 10.3 | 5 | 89 |
| Example 32 | 9.6 | 5 | 88 |

TABLE 10-continued

| Examples | | | |
|---|---|---|---|
| Example 33 | 10.5 | 5 | 87 |
| Example 34 | 9.3 | 5 | 89 |
| Example 35 | 10.1 | 5 | 86 |
| Example 36 | 9.6 | 5 | 85 |
| Example 37 | 9.9 | 5 | 86 |
| Example 38 | 10.2 | 4 | 82 |

Properties of black magnetic toner

| Examples | Volume resistivity value ($\Omega \cdot cm$) | Magnetic properties Coercive force value (kA/m) | (Oe) |
|---|---|---|---|
| Example 27 | $5.6 \times 10^{13}$ | 7.9 | 99 |
| Example 28 | $6.8 \times 10^{13}$ | 4.6 | 58 |
| Example 29 | $9.3 \times 10^{13}$ | 25.5 | 321 |
| Example 30 | $1.4 \times 10^{14}$ | 4.1 | 51 |
| Example 31 | $5.1 \times 10^{13}$ | 8.0 | 101 |
| Example 32 | $1.0 \times 10^{14}$ | 4.8 | 60 |
| Example 33 | $5.9 \times 10^{13}$ | 25.1 | 316 |
| Example 34 | $8.3 \times 10^{13}$ | 4.0 | 50 |
| Example 35 | $5.1 \times 10^{13}$ | 7.9 | 99 |
| Example 36 | $6.4 \times 10^{13}$ | 8.0 | 100 |
| Example 37 | $1.0 \times 10^{14}$ | 7.6 | 96 |
| Example 38 | $2.7 \times 10^{13}$ | 7.8 | 98 |

Properties of black magnetic toner
Magnetic properties
Saturation magnetization value

| Examples | (795.8 kA/m) (10 kOe) (Am²/kg) | (emu/g) | (79.6 kA/m) (1 kOe) (Am²/kg) | (emu/g) |
|---|---|---|---|---|
| Example 27 | 31.6 | 31.6 | 22.1 | 22.1 |
| Example 28 | 30.3 | 30.3 | 21.6 | 21.6 |
| Example 29 | 29.6 | 29.6 | 22.6 | 22.6 |
| Example 30 | 31.6 | 31.6 | 23.1 | 23.1 |
| Example 31 | 32.1 | 32.1 | 21.6 | 21.6 |
| Example 32 | 30.8 | 30.8 | 20.8 | 20.8 |
| Example 33 | 31.4 | 31.4 | 19.6 | 19.6 |
| Example 34 | 31.6 | 31.6 | 20.3 | 20.3 |
| Example 35 | 31.3 | 31.3 | 21.2 | 21.2 |
| Example 36 | 32.1 | 32.1 | 20.9 | 20.9 |
| Example 37 | 30.6 | 30.6 | 22.1 | 22.1 |
| Example 38 | 31.9 | 31.9 | 21.9 | 21.9 |

Properties of black magnetic toner
Magnetic properties
Residual magnetization value

| Examples | (795.8 kA/m) (10 kOe) (Am²/kg) | (emu/g) | (79.6 kA/m) (1 kOe) (Am²/kg) | (emu/g) | Blackness (L* value) (−) |
|---|---|---|---|---|---|
| Example 27 | 4.3 | 4.3 | 3.9 | 3.9 | 17.8 |
| Example 28 | 3.2 | 3.2 | 2.6 | 2.6 | 17.1 |
| Example 29 | 9.6 | 9.6 | 7.6 | 7.6 | 17.5 |
| Example 30 | 3.9 | 3.9 | 2.9 | 2.9 | 18.5 |
| Example 31 | 4.2 | 4.2 | 3.8 | 3.8 | 17.2 |
| Example 32 | 3.0 | 3.0 | 2.7 | 2.7 | 18.0 |
| Example 33 | 10.0 | 10.0 | 7.8 | 7.8 | 17.9 |
| Example 34 | 3.6 | 3.6 | 2.6 | 2.6 | 18.5 |
| Example 35 | 4.0 | 4.0 | 3.7 | 3.7 | 17.6 |
| Example 36 | 4.1 | 4.1 | 3.8 | 3.8 | 17.7 |
| Example 37 | 4.0 | 4.0 | 3.7 | 3.7 | 17.6 |
| Example 38 | 4.0 | 4.0 | 3.7 | 3.7 | 18.3 |

TABLE 11

Properties of black magnetic toner

| Comparative Examples | Average particle size (μm) | Dispersibility (−) | Fluidity index (−) |
|---|---|---|---|
| Comparative Example 12 | 10.0 | 3 | 51 |
| Comparative Example 13 | 10.1 | 3 | 53 |
| Comparative Example 14 | 9.9 | 3 | 50 |
| Comparative Example 15 | 10.2 | 3 | 53 |
| Comparative Example 16 | 10.1 | 2 | 62 |
| Comparative Example 17 | 10.4 | 3 | 56 |
| Comparative Example 18 | 9.5 | 3 | 57 |
| Comparative Example 19 | 10.3 | 3 | 59 |
| Comparative Example 20 | 10.0 | 3 | 59 |
| Comparative Example 21 | 9.3 | 3 | 55 |
| Comparative Example 22 | 10.1 | 3 | 56 |
| Comparative Example 23 | 10.0 | 3 | 60 |

Properties of black magnetic toner

| Comparative Examples | Volume resistivity value ($\Omega \cdot cm$) | Magnetic properties Coercive force value (kA/m) | (Oe) |
|---|---|---|---|
| Comparative Example 12 | $6.5 \times 10^{12}$ | 8.2 | 103 |
| Comparative Example 13 | $5.7 \times 10^{12}$ | 4.9 | 61 |
| Comparative Example 14 | $9.8 \times 10^{11}$ | 27.0 | 339 |
| Comparative Example 15 | $3.7 \times 10^{12}$ | 4.0 | 50 |
| Comparative Example 16 | $6.3 \times 10^{12}$ | 8.0 | 101 |
| Comparative Example 17 | $8.6 \times 10^{11}$ | 8.0 | 100 |
| Comparative Example 18 | $4.3 \times 10^{12}$ | 7.8 | 98 |
| Comparative Example 19 | $9.8 \times 10^{11}$ | 8.2 | 103 |
| Comparative Example 20 | $4.6 \times 10^{12}$ | 8.0 | 101 |
| Comparative Example 21 | $3.1 \times 10^{11}$ | 7.6 | 96 |
| Comparative Example 22 | $4.7 \times 10^{11}$ | 7.7 | 97 |
| Comparative Example 23 | $2.6 \times 10^{12}$ | 8.0 | 101 |

Properties of black magnetic toner
Magnetic properties
Saturation magnetization value

| Comparative Examples | (795.8 kA/m) (10 kOe) (Am²/kg) | (emu/g) | (79.6 kA/m) (1 kOe) (Am²/kg) | (emu/g) |
|---|---|---|---|---|
| Comparative Example 12 | 39.5 | 39.5 | 30.0 | 30.0 |
| Comparative Example 13 | 38.7 | 38.7 | 29.2 | 29.2 |
| Comparative Example 14 | 37.5 | 37.5 | 28.9 | 28.9 |
| Comparative | 34.6 | 34.6 | 26.0 | 26.0 |

TABLE 11-continued

| | | | | |
|---|---|---|---|---|
| Example 15 | | | | |
| Comparative Example 16 | 30.2 | 30.2 | 20.8 | 20.8 |
| Comparative Example 17 | 30.3 | 30.3 | 19.6 | 19.6 |
| Comparative Example 18 | 30.6 | 30.6 | 20.3 | 20.3 |
| Comparative Example 19 | 29.6 | 29.6 | 20.4 | 20.4 |
| Comparative Example 20 | 29.3 | 29.3 | 20.1 | 20.1 |
| Comparative Example 21 | 30.1 | 30.1 | 19.9 | 19.9 |
| Comparative Example 22 | 30.2 | 30.2 | 20.1 | 20.1 |
| Comparative Example 23 | 29.6 | 29.6 | 20.9 | 20.9 |

| | Properties of black magnetic toner | | | |
|---|---|---|---|---|
| | Magnetic properties Residual magnetization value | | | |
| Comparative | (795.8 kA/m) (10 kOe) | | (79.6 kA/m) (1 kOe) | | Blackness (L* value) |
| Examples | (Am²/kg) | (emu/g) | (Am²/kg) | (emu/g) | (-) |
| Comparative Example 12 | 5.4 | 5.4 | 4.2 | 4.2 | 22.4 |
| Comparative Example 13 | 3.6 | 3.6 | 2.7 | 2.7 | 22.2 |
| Comparative Example 14 | 12.8 | 12.8 | 9.5 | 9.5 | 26.1 |
| Comparative Example 15 | 3.9 | 3.9 | 3.1 | 3.1 | 34.9 |
| Comparative Example 16 | 4.3 | 4.3 | 3.5 | 3.5 | 20.1 |
| Comparative Example 17 | 4.2 | 4.2 | 3.3 | 3.3 | 21.2 |
| Comparative Example 18 | 4.2 | 4.2 | 3.5 | 3.5 | 20.9 |
| Comparative Example 19 | 4.1 | 4.1 | 3.4 | 3.4 | 21.3 |
| Comparative Example 20 | 4.1 | 4.1 | 3.3 | 3.3 | 20.6 |
| Comparative Example 21 | 4.3 | 4.3 | 3.2 | 3.2 | 21.0 |
| Comparative Example 22 | 4.2 | 4.2 | 3.3 | 3.3 | 20.8 |
| Comparative Example 23 | 4.1 | 4.1 | 3.2 | 3.2 | 20.6 |

What is claimed is:

1. A black magnetic toner having a volume resistivity of $1.0 \times 10^{13}$ to $1.0 \times 10^{17}$ Ωcm, comprising:
   a binder resin, and
   black magnetic composite particles having an average particle diameter of 0.06 to 1.0 μm, comprising:
   magnetic iron oxide particles;
   a coating layer formed on the surface of said magnetic iron oxide particle, comprising at least one organosilicon compound selected from the group consisting of:
   (1) organosilane compounds obtained from an alkoxysilane compounds, and
   (2) polysiloxanes or modified polysiloxanes; and
   a carbon black coat formed on said coating layer comprising said organosilicon compound, in an amount of 26 to 55 parts by weight based on 100 parts by weight of said magnetic iron oxide particles.

2. A black magnetic toner according to claim 1, wherein the amount of the binder resin is 50 to 900 parts by weight based on 100 parts by weight of the black magnetic composite particles.

3. A black magnetic toner according to claim 1, which further comprises an average particle size of 3 to 15 μm.

4. A black magnetic toner according to claim 1, which further comprises a fluidity index of 78 to 100.

5. A black magnetic toner according to claim 1, which further comprises a blackness (L* value) of not more than 19.

6. A black magnetic toner according to claim 1, wherein said magnetic iron oxide particles are particles having a coat formed on at least a part of the surface of said magnetic iron oxide particles and comprising at least one compound selected from the group consisting of hydroxides of aluminum, oxides of aluminum, hydroxides of silicon and oxides of silicon in an amount of 0.01 to 50% by weight, calculated as Al or $SiO_2$, based on the total weight of the magnetic iron oxide particles.

7. A black magnetic toner according to claim 1, wherein said modified polysiloxanes are ones selected from the group consisting of:
   (A) polysiloxanes modified with at least one compound selected from the group consisting of polyethers, polyesters and epoxy compounds, and
   (B) polysiloxanes whose molecular terminal is modified with at least one group selected from the group consisting of carboxylic acid groups, alcohol groups and a hydroxyl group.

8. A black magnetic toner according to claim 7, wherein said polysiloxanes modified with at least one compound selected from the group consisting of polyethers, polyesters and epoxy compounds are represented by the general formula (III), (IV) or (V):

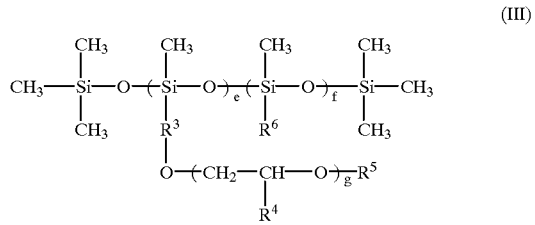

(III)

wherein $R^3$ is $-(-CH_2-)_h-$; $R^4$ is $-(-CH_2-)_i-CH_3$; $R^5$ is $-OH$, $-COOH$, $-CH=CH_2$, $-C(CH_3)=CH_2$ or $-(-CH_2-)_j-CH_3$; $R^6$ is $-(-CH_2-)_k-CH_3$; g and h are an integer of 1 to 15; i, j and k are an integer of 0 to 15; e is an integer of 1 to 50; and f is an integer of 1 to 300;

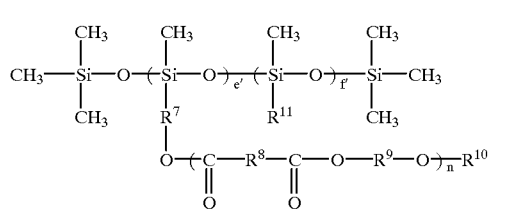

(IV)

wherein $R^7$, $R^8$ and $R^9$ are $-(-CH_2-)_q-$ and may be the same or different; $R^{10}$ is $-OH$, $-COOH$, $-CH=CH_2$, $-C(CH_3)=CH_2$ or $-(-CH_2-)_r-CH_3$; $R^{11}$ is $-(-CH_2-)_s-CH_3$; n and q are an integer of 1 to 15; r and s are an integer of 0 to 15; e' is an integer of 1 to 50; and f' is an integer of 1 to 300; or (V)

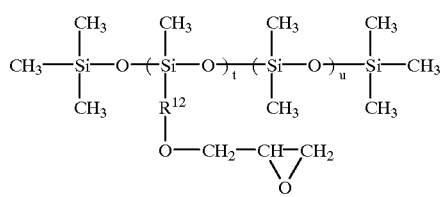

wherein $R^{12}$ is —(—$CH_2$—)$_v$—; v is an integer of 1 to 15; t is an integer of 1 to 50; and u is an integer of 1 to 300.

9. A black magnetic toner according to claim 7, wherein said polysiloxanes whose molecular terminal is modified with at least one group selected from the group consisting of carboxylic acid groups, alcohol groups and a hydroxyl group are represented by the general formula (VI):

(VI)

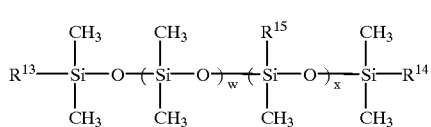

wherein $R^{13}$ and $R^{14}$ are —OH, $R^{16}$OH or $R^{17}$COOH and may be the same or different; $R^{15}$ is —$CH_3$ or —$C_6H_5$; $R^{16}$ and $R^{17}$ are —(—$CH_2$—)$_y$—; y is an integer of 1 to 15; w is an integer of 1 to 200; and x is an integer of 0 to 100.

10. A black magnetic toner according to claim 1, wherein said alkoxysilane compound is represented by the general formula (I):

 (I)

wherein $R^1$ is $C_6H_5$—, $(CH_3)_2CHCH_2$— or n-$C_bH_{2b+1}$— (wherein b is an integer of 1 to 18); X is $CH_3O$— or $C_2H_5O$—; and a is an integer of 0 to 3.

11. A black magnetic toner according to claim 10, wherein said alkoxysilane compound is methyl triethoxysilane, dimethyl diethoxysilane, phenyl triethoxysilane, diphenyl diethoxysilane, methyl trimethoxysilane, dimethyl dimethoxysilane, phenyl trimethoxysilane, diphenyl dimethoxysilane, isobutyl trimethoxysilane or decyl trimethoxysilane.

12. A black magnetic toner according to claim 1, wherein said polysiloxanes are represented by the general formula (II):

(II)

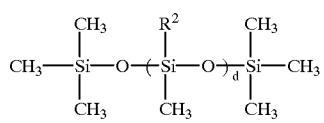

wherein $R^2$ is H— or $CH_3$—, and d is an integer of 15 to 450.

13. A black magnetic toner according to claim 12, wherein said polysiloxanes are ones having methyl hydrogen siloxane units.

14. A black magnetic toner according to claim 1, wherein the amount of said coating organosilicon compounds is 0.02 to 5.0% by weight, calculated as Si, based on the total weight of the organosilicon compounds and said magnetic iron oxide particles.

15. A black magnetic toner according to claim 1, wherein the thickness of said carbon black coat is not more than 0.06 μm.

16. A black magnetic toner according to claim 1, wherein said black magnetic composite particles have a geometrical standard deviation of particle sizes of 1.01 to 2.0.

17. A black magnetic toner according to claim 1, wherein said black magnetic composite particles have a BET specific surface area value of 1 to 100 m²/g, a fluidity index of 48 to 90 and a blackness (L* value) of 15 to 19.5.

18. A black magnetic toner according to claim 1, wherein said black magnetic composite particles have a coercive force of 0.8 to 31.8 kA/m, a saturation magnetization of 50 to 91 Am²/kg, and a residual magnetization of 1 to 35 Am²/kg.

19. Black magnetic composite particles for a black magnetic toner, comprising:

magnetic iron oxide particles having an average major axis diameter of 0.005 to 0.95 μm;

a coating layer formed on the surface of said magnetic iron oxide particles, comprising at least one organosilicon compound selected from the group consisting of:

(1) organosilane compounds obtained from an alkoxysilane compounds, and (2) polysiloxanes or modified polysiloxanes; and a carbon coat composed of at least two carbon black layers internally adhered with other through an adhesive, formed on said coating layer comprising said organosilicon compound, in an amount of 26 to 55 parts by weight based on 100 parts by weight of said magnetic iron oxide particles.

20. Black magnetic composite particles according to claim 19, wherein said magnetic iron oxide particles are particles having a coat formed on at least a part of the surface of said magnetic iron oxide particles and comprising at least one compound selected from the group consisting of hydroxides of aluminum, oxides of aluminum, hydroxides of silicon and oxides of silicon in an amount of 0.01 to 50% by weight, calculated as Al or $SiO_2$, based on the total weight of the magnetic iron oxide particles.

21. Black magnetic composite particles according to claim 19, wherein said modified polysiloxanes are ones selected from the group consisting of:

(A) polysiloxanes modified with at least one compound selected from the group consisting of polyethers, polyesters and epoxy compounds, and (B) polysiloxanes whose molecular terminal is modified with at least one group selected from the group consisting of carboxylic acid groups, alcohol groups and a hydroxyl group.

22. Black magnetic composite particles according to claim 21, wherein said polysiloxanes modified with at least one compound selected from the group consisting of polyethers, polyesters and epoxy compounds are represented by the general formula (III), (IV) or (V):

(III)

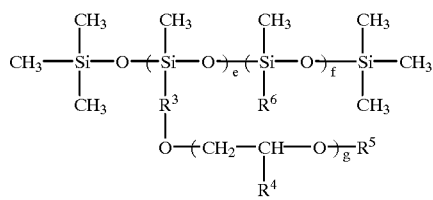

wherein $R^3$ is —$(-CH_2-)_h$—; $R^4$ is —$(-CH_2-)_i$—$CH_3$; $R^5$ is —OH, —COOH, —CH=$CH_2$, —C($CH_3$)=$CH_2$ or —$(-CH_2-)_j$—$CH_3$; $R^6$ is —$(-CH_2-)_k$—$CH_3$; g and h are an integer of 1 to 15; i, j and k are an integer of 0 to 15; e is an integer of 1 to 50; and f is an integer of 1 to 300;

(IV)

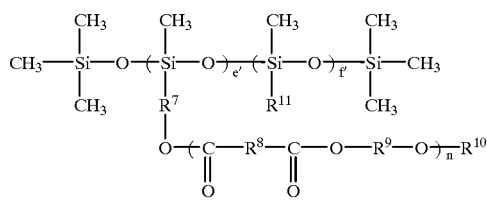

wherein $R^7$, $R^8$ and $R^9$ are —$(-CH_2-)_q$— and may be the same or different; $R^{10}$ is —OH, —COOH, —CH=$CH_2$, —C($CH_3$)=$CH_2$ or —$(-CH_2-)_r$—$CH_3$; $R^{11}$ is —$(-CH_2-)_s$—$CH_3$; n and q are an integer of 1 to 15; r and s are an integer of 0 to 15; e' is an integer of 1 to 50; and f' is an integer of 1 to 300; or (V)

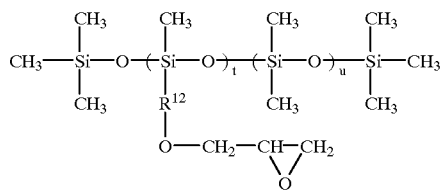

wherein $R^{12}$ is —$(-CH_2-)_v$—; v is an integer of 1 to 15; t is an integer of 1 to 50; and u is an integer of 1 to 300.

23. Black magnetic composite particles according to claim 21, wherein said polysiloxanes whose molecular terminal is modified with at least one group selected from the group consisting of carboxylic acid groups, alcohol groups and a hydroxyl group are represented by the general formula (VI):

(VI)

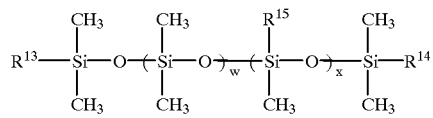

wherein $R^{13}$ and $R^{14}$ are —OH, $R^{16}$OH or $R^{17}$COOH and may be the same or different; $R^{15}$ is —$CH_3$ or —$C_6H_5$; $R^{16}$ and $R^{17}$ are —$(-CH_2-)_y$—; y is an integer of 1 to 15; w is an integer of 1 to 200; and x is an integer of 0 to 100.

24. Black magnetic composite particles according to claim 19, wherein said alkoxysilane compound is represented by the general formula (I):

$$R^1{}_aSiX_{4-a} \qquad (I)$$

wherein $R^1$ is $C_6H_5$—, $(CH_3)_2CHCH_2$— or n-$C_bH_{2b+1}$— (wherein b is an integer of 1 to 18); X is $CH_3O$— or $C_2H_5O$—; and a is an integer of 0 to 3.

25. Black magnetic composite particles according to claim 24, wherein said alkoxysilane compound is methyl triethoxysilane, dimethyl diethoxysilane, phenyl triethoxysilane, diphenyl diethoxysilane, methyl trimethoxysilane, dimethyl dimethoxysilane, phenyl trimethoxysilane, diphenyl dimethoxysilane, isobutyl trimethoxysilane or decyl trimethoxysilane.

26. Black magnetic composite particles according to claim 19, wherein said polysiloxanes are represented by the general formula (II):

(II)

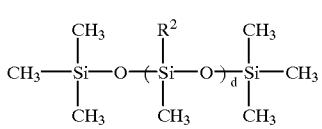

wherein $R^2$ is H— or $CH_3$—, and d is an integer of 15 to 450.

27. Black magnetic composite particles according to claim 26, wherein said polysiloxanes are ones having methyl hydrogen siloxane units.

28. Black magnetic composite particles according to claim 19, wherein the amount of said coating organosilicon compounds is 0.02 to 5.0% by weight, calculated as Si, based on the total weight of the organosilicon compounds and said magnetic iron oxide particles.

29. Black magnetic composite particles according to claim 19, wherein the thickness of said carbon black coat is not more than 0.06 μm.

30. Black magnetic composite particles according to claim 19, wherein the average particle size is 0.06 to 1.0 μm.

31. Black magnetic composite particles according to claim 19, wherein the geometrical standard deviation of particle sizes is 1.01 to 2.0.

32. Black magnetic composite particles according to claim 19, wherein the BET specific surface area value is 1 to 100 m²/g, the fluidity index is 48 to 90 and the blackness (L* value) is 15 to 19.5.

33. Black magnetic composite particles according to claim 19, wherein the coercive force is 0.8 to 31.8 kA/m, the saturation magnetization is 50 to 91 Am²/kg, and the residual magnetization is 1 to 35 Am²/kg.

* * * * *